United States Patent [19]

Nakayama et al.

[11] Patent Number: 5,730,149
[45] Date of Patent: Mar. 24, 1998

US005730149A

[54] TOILET-BOWL-MOUNTED URINALYSIS UNIT

[75] Inventors: Chiaki Nakayama; Kuniaki Shinohara; Takanori Matsuno; Toshio Koguro; Hiroshi Tsuboi; Yukihiro Fukuda; Naoki Sato, all of Kita-kyushu, Japan

[73] Assignee: Toto Ltd., Fukuoka, Japan

[21] Appl. No.: 507,420

[22] PCT Filed: Dec. 27, 1994

[86] PCT No.: PCT/JP94/02264

§ 371 Date: Nov. 3, 1995

§ 102(e) Date: Nov. 3, 1995

[87] PCT Pub. No.: WO95/18373

PCT Pub. Date: Jul. 6, 1995

[30] Foreign Application Priority Data

| Dec. 30, 1993 | [JP] | Japan | 5-354281 |
| Dec. 30, 1993 | [JP] | Japan | 5-354282 |
| Dec. 30, 1993 | [JP] | Japan | 5-354283 |
| Dec. 30, 1993 | [JP] | Japan | 5-354284 |
| Mar. 31, 1994 | [JP] | Japan | 6-087399 |

[51] Int. Cl.[6] ............................................. A61B 5/00
[52] U.S. Cl. ................................... 128/760; 128/771
[58] Field of Search ................................... 128/760, 771; 4/314, 661; 73/864.81–864.85

[56] References Cited

U.S. PATENT DOCUMENTS

| 4,636,474 | 1/1987 | Ogura et al. . | |
| 4,860,767 | 8/1989 | Maekawa | 128/760 |
| 4,901,736 | 2/1990 | Huang | 128/760 |
| 4,961,431 | 10/1990 | Ikenaga et al. . | |
| 4,962,550 | 10/1990 | Ikenaga et al. . | |
| 4,982,741 | 1/1991 | Saito et al. . | |
| 5,073,500 | 12/1991 | Saito et al. . | |
| 5,111,539 | 5/1992 | Hiruta et al. . | |
| 5,184,359 | 2/1993 | Tsukamura et al. . | |
| 5,198,192 | 3/1993 | Saito et al. | 128/760 |

FOREIGN PATENT DOCUMENTS

| 59-217844 | 12/1984 | Japan . |
| 60-117155 | 6/1985 | Japan . |
| 63-6291 | 2/1988 | Japan . |
| 1-136573 | 9/1989 | Japan . |
| 2-193054 | 7/1990 | Japan . |
| 3-139334 | 6/1991 | Japan . |
| 4-77662 | 3/1992 | Japan . |
| 4-366743 | 12/1992 | Japan . |
| 5-7767 | 2/1993 | Japan . |
| 5-19341 | 4/1993 | Japan . |
| 5-30764 | 4/1993 | Japan . |
| 6-87400 | 3/1994 | Japan . |
| 6-230006 | 8/1994 | Japan . |
| 6-258315 | 9/1994 | Japan . |
| 6-258316 | 9/1994 | Japan . |
| 7-35745 | 2/1995 | Japan . |

*Primary Examiner*—Max Hindenburg
*Attorney, Agent, or Firm*—Finnegan, Henderson, Farabow, Garrett & Dunner, L.L.P.

[57] ABSTRACT

A toilet bowl-mounted urinalysis unit (14) adapted to be readily mounted to a standard water closet bowl fixture (12) for sampling and analysis of urine at a toilet. The unit (14) includes a substantially self-contained housing (22) which is designed to be mounted on the upper surface of the standard bowl fixture (12) between the bowl (16) and the flushing water supply section (18). Hinged to the housing (22) is a toilet seat (24) to which is mounted a urine sampling device (26) designed such that urine excreted into the bowl (16) is sampled in mid-air within the inner space of the bowl. The housing (22) receives a urinalysis device (50) with a polarographic flow cell and a syringe pump (52) for transferring a urine sample to the flow cell together with a carrier liquid. The polarographic flow cell has a working electrode supporting an enzyme. In one embodiment, a reservoir for the carrier liquid is received within the housing (22). In another embodiment, the carrier liquid reservoir (402) is mounted to a toilet lid. A method for reforming a toilet equipped with a standard bowl fixture (12) into a toilet equipped with a urinalysis function is also provided wherein a prefabricated toilet seat assembly (28) having the urine sampling device (26) incorporated in advance into the toilet seat (24) is used.

79 Claims, 25 Drawing Sheets

TOILET-BOWL-MOUNTED URINALYSIS UNIT

This application is a 371 of PCT/JP94/02264 filed on Dec. 27, 1994.

1. Technical Field

The present invention relates to a toilet provided with a urine analysis function which is capable of sampling and analyzing, in situ, urine excreted by the individuals at a toilet installed in residences, offices or other facilities. More specifically, the present invention relates to a toilet bowl-mounted urinalysis unit which is adapted to be mounted to a standardized water closet bowl fixture commercially available on the market. The present invention is also concerned with a method for converting a toilet equipped with a standard toilet bowl fixture to a toilet having a urinalysis function.

2. Background Art

In view of the trends for longevity of the individuals, the importance of health care and maintenance has been receiving increasing attention. As urine is an important source of information that represents the health conditions of an individual, various dysfunction such as pancreatic disorders (typically, diabetes), hypohepatia, and kidney disorders can be detected advantageously in a non-invasive manner by performing quantitative analysis of certain urine constituents, such as glucose, protein, urobilinogen, occult blood and other substances. Accordingly, proposed in the art are toilets having a urinalysis function which are capable of performing sampling and analysis of urine so as to assist the individuals in rendering their health check by making use of toilets provided in residences, offices and other facilities.

For instance, JP-A-59-217844 of Toto Ltd., U.S. Pat. No. 4,961,431 to Ikenaga et al., U.S. Pat. No. 4,962,550 to Ikenaga et al., U.S. Pat. No. 4,982,741 to Saito et al., U.S. Pat. No. 5,073,500 to Saito et al., U.S. Pat. No. 5,111,539 to Hiruta et al., and U.S. Pat. No. 5,184,359 to Tsutamura et al., propose to form a urine sampling cavity or sampling well on the bowl surface of a water closet bowl fixture to sample a quantity of urine excreted into the toilet bowl, the urine sample being subjected to urinalysis by way of liquid chromatographic process, colorimetric analysis process, or polarographic or voltammetric process.

The advantage of these sampling systems which are designed to make use of the urine sampling cavity or sampling well formed on the bowl surface is that urine excreted into the toilet bowl is received and collected by a considerably wide surface area of the bowl so that urine is readily sampled regardless of the direction of urination or the variation in the trajectory of urine column. Therefore, an adequate quantity of urine necessary for urinalysis can easily be sampled even in the case of elderly people who are apt to suffer from the shortage of the amount of urine per urination.

However, the problem associated with these systems is that they require a special-purpose toilet bowl fixture provided with a urine sampling cavity or well formed on the bowl surface for the purposes of sampling of urine so that a standard-type toilet bowl fixture having the conventional bowl configuration cannot be used. Accordingly, in order to reform an existing toilet equipped with the conventional standard bowl fixture into a toilet having a urinalysis function, the existing conventional bowl fixture must first be removed and then a special purpose bowl fixture envisioned for sampling and urinalysis must be installed. This involves a great deal of labor and expenses for reform works and necessitates to discard the existing bowl fixture.

Furthermore, as such special purpose toilet bowl fixtures must be manufactured specially and separately from standard-type toilet bowls, it is difficult to produce them via the mass production process. As a result, these systems are too expensive to be installed widely in regular households and offices.

Another disadvantage is the difficulty in obtaining a good urine specimen since residual flushing water remaining in the urine sampling cavity of the bowl surface after flushing of the bowl tends to dilute the fresh urine to be sampled. Similarly, the fresh urine sample is susceptible to contamination by residual urine and feces since the urine sampling section is formed on the bowl surface.

JP-A-3-139334 of Matsushita Denko K.K. discloses a urine sampling and analyzing apparatus having a wheeled main body which is intended to be pulled aside of the toilet bowl fixture when in use and to be moved away into a non-obstructive location such as the corner of the toilet room when not in use. The main body supports a urine sampling cup in a telescoping fashion so that, when urine is to be sampled, the urine sampling cup is moved into the bowl through a gap defined between the toilet bowl and the toilet seat. A testing strip is dipped into the urine sample sampled by the sampling cup and is tested for urinalysis.

The advantage of this apparatus is that urine can be sampled by using a standard-type toilet bowl fixture.

However, the problem involved in this apparatus is that the wheeled main body as placed on the toilet floor occupies the toilet floor and therefore hinders cleaning of the toilet as well as routine use of the toilet for the purposes of excretion. Handling and manipulation of the apparatus is cumbersome because, each time the apparatus is used, the main body must be moved toward and away from the toilet bowl in order to position the apparatus in a non-obstructive location after use.

Furthermore, the position of the sampling cup is so high that the cup interferes with or comes too close to the body of the user as seated on the toilet seat because the sampling cup is inserted through the gap between the bowl and the toilet seat in the lateral direction to extend above the bowl. Moreover, the user must control the position of the main body of the apparatus by the hands to ensure that the sampling cup is properly positioned to meet the trajectory of falling urine. As a result, sampling of urine is extremely difficult to perform so that there is a risk of failure of sampling. Another disadvantage is that use of testing strips is not suitable to perform a high degree of quantitative analysis and requires disposal of the used testing strips which is often cumbersome.

U.S. Pat. No. 4,636,474 to Ogura et al., JP-A-60-117115 of Toshiba K.K., and JP-U-1-136573 of Matsushita Denko K.K. disclose urinalysis apparatus wherein a swingable arm is mounted for pivoting movement to a toilet seat, with a urine sensor being arranged at the free end of the arm to analyze urine upon contact with urine excreted into the bowl. These apparatus also enjoy the advantage that they can be used in combination with the standard toilet bowl fixtures.

However, contacting the sensor directly with the original urine gives rise to several problems. Thus, in contrast to diagnosis by way of blood wherein the hydrogen ion concentration (pH), the chlorine ion concentration and the oxygen concentration are constantly conditioned to a high degree by various physiological organs, urine as an excrement from the human body is subject to a wide range of variations in the pH, the chlorine ion concentration and the oxygen concentration from sample to sample so that it is difficult to perform a high degree of analysis for a particular urinal constituent unless urine as sampled is diluted by a buffer. In addition, contacting the sensor directly with the original urine without dilution causes premature degradation of the sensor and reduces the service life thereof. Further, it is impossible to perform urinalysis for a plurality of items because it is difficult to arrange a plurality of sensors at the end of the swingable arm.

JP-U-5-30764 of NOK K.K. proposes a health diagnostic apparatus which is adapted to sample a quantity of urine by a urine sampling mechanism attached to a toilet seat and to transfer it to an analyzer station for urinalysis. In order to sample urine excreted from the user seated on the toilet seat by receiving it in mid air within the toilet bowl, a swingable arm is pivoted at an end thereof to the underside of the toilet seat for swinging movement about a vertical axis, the other end of the arm being provided with an elongated urine sampling cup. There is described that the arm may be rotated manually or electrically.

Urine sampled by the sampling cup is drawn by a manual or automatic syringe and, after being mixed with liquid reagent, is forwarded to the measuring station including an absorption spectrophotometer in which it is subjected to analysis. It is considered that the measuring station receiving the receptacles for reagent, various pumps and the absorption spectrophotometer is arranged adjacent the toilet seat at a side thereof and is placed on the toilet floor. It is described that the liquid reagents must be kept in a refrigerator when not in use.

This health diagnostic apparatus also enjoys the advantage of sampling urine by making use of an existing or standard toilet bowl fixture without requiring a specially-fabricated toilet bowl fixture, since urine is sampled in mid air by the sampling cup which is moved within the inner space of the bowl. Furthermore, a high degree of analysis can be achieved as urine specimen is subjected to analysis after being diluted by the liquid reagent.

Nevertheless, similar to the arrangement of JP-A-3-139334, this apparatus suffers from the inconvenience that cleaning and routine use of the toilet are hindered because the measuring station receiving the reagent receptacles and the absorption spectrophotometer is placed on the toilet floor. Accordingly, the toilet is not easy to use. Further, operation and maintenance of the apparatus are burdensome since the reagents must be stored in a refrigerator. As liquid reagents are expensive, a high running cost is incurred.

Another problem of this apparatus is that it is difficult to realize a commercially feasible form of the urine sampling mechanism. That is, for the urine sampling mechanism to be commercially feasible, several performances must be fulfilled. First, it is desirable that urine be reliably and readily sampled without loosing the chance of sampling, regardless of the fluctuation in the trajectory of urine column that would result due to the sexual difference of the user or due to the variation in the posture of the user as seated on the toilet seat. This is particularly important when the total quantity of urine per urination is limited as is the case of elderly people. In the urine sampling mechanism disclosed in JP-U-5-30764, it is difficult to sample urine with certainty since the urine sampling cup is moved along an arcuate path around a vertical pivot axis and, therefore, cannot be accommodated to the variation in the position of falling urine column that may occur in the fore-and-aft direction. It is also desirable that the urine sampling cup do not interfere with the user's body as it is rotated and retracted, that the sampling cup be washed and cleansed after use, that the sampling cup held in its retracted position be not contaminated, and that the toilet seat present a neat appearance when swung up for male urination.

Furthermore, it is desirable that the urine sampling mechanism can be mounted to the toilet seat without difficulty and without impairing the mechanical strength and sealability of the seat. In this regard, however, severe designing requirements are imposed when a urine sampling mechanism is to be installed to an existing toilet seat. Thus, in a commercially-available standard toilet, only a limited gap as small as about 1.5–2 cm is available between the lower surface of the toilet seat and the upper surface of the rim of the toilet bowl. The radial space available within the bowl to arrange the urine sampling mechanism is also limited. As a result, in order to install a urine sampling mechanism by utilizing such extremely narrow limited gap and space, severe dimensional restrictions and restraints are imposed on the design of the urine sampling mechanism. If the urine sampling mechanism were designed small enough to be readily accommodated within such a narrow gap, the urine sampling mechanism would become quite refined and delicate so that the durability of the movable parts thereof and the reliability of operation would be decreased. In addition, as the urine sampling cup is made smaller, the aperture thereof for receiving urine would be reduced which, in turn, decreases the probability of urine sampling. Accordingly, the probability of sampling must be sacrificed if the urine sampling mechanism is to be made small and compact.

If, to the contrary, the urine sampling mechanism is to be made larger, then an existing toilet seat must be subjected to substantial processing and machining works, such as by cutting away a part thereof, in order to install the mechanism in a swingable manner within the narrow space defined between the lower surface of the toilet seat and the upper surface of the rim of the toilet bowl. In that event, reforming of an existing toilet to add the urinalysis function would be complicated and difficult to perform thereby increasing the amount of work and expense involved. In addition, by tampering with the toilet seat, the reliability of the operation of the urine sampling mechanism is reduced and the mechanical strength of the seat is impaired.

Accordingly, the primary object of the present invention is to provide a urinalysis unit which is capable of performing sampling and analysis of urine by making use of a toilet equipped with a conventional standard water closet bowl fixture and which can be readily mounted to the standard water closet bowl fixture and is easy to use.

Another object of the invention is to provide a urinalysis unit of the type adapted to be installed to a standard water closet bowl fixture and which does not obstruct cleaning and routine use of the toilet.

A still another object of the invention is to provide a urinalysis unit of the type mentioned which is able to perform a high degree of urinalysis, which is easy to maintain and which is yet operable at a reduced running costs.

A further object of the invention is to provide a urinalysis unit of the type mentioned which is capable of readily sampling urine with reliability.

Another object of the invention is to provide a urinalysis unit of the type mentioned which is provided with a commercially feasible urine sampling mechanism.

Another object of the invention is to provide a urinalysis unit which is compact in size and which is capable of being readily mounted to a standard water closet bowl fixture.

Another object of the present invention is to provide a method for reforming and converting an existing toilet equipped with a standard water closet bowl fixture into a toilet having a urinalysis function, which method is easy to carry out yet retaining the ease of use of the toilet and the operational reliability of the urine sampling mechanism.

Disclosure of the Invention

The present invention provides a toilet bowl-mounted urinalysis unit for sampling and analyzing urine at a toilet equipped with a conventional standard water closet bowl fixture. One of the features of the invention is that the urinalysis unit comprises a substantially self-contained housing which houses or supports the major component parts of the unit and that the housing is adapted to be readily mounted to the standard water closet bowl fixture.

More specifically, the housing is adapted to be mounted on the upper surface of the standard bowl fixture between the bowl and the flushing water supply section thereof. A toilet seat is swingably hinged to the housing. A urine sampling device having a movable urine sampling vessel is incorporated in the toilet seat for sampling, in mid air within the inner space of the bowl, a quantity of urine excreted into the bowl, the urine sampling device being movable conjointly with the toilet seat. The urinalysis unit may further comprise a urinalysis device, a fluid transfer device with a fluid pump for transferring urine sample from the sampling vessel to the urinalysis device, an output device for outputting the results of urinalysis, and a control device. Among these component parts of the unit, the urinalysis device and the fluid pump of the fluid transfer device may be arranged in the housing.

As in this manner the movable urine sampling vessel is supported by the toilet seat to sample urine in mid air within the inner space of the bowl, a special purpose toilet bowl fixture which is specifically designed for sampling of urine is not required so that urine can be sampled by making use of a toilet provided with the conventional standard bowl fixture. As the housing receiving the urinalysis device and the fluid pump is mounted on the upper surface of the bowl fixture between the bowl and the flushing water supply section, the housing does not interfere with the toilet floor and leaves the floor free and open. Accordingly, the urinalysis unit according to the invention does not hinder cleaning and routine use of the toilet.

Since the housing, which supports the toilet seat incorporating the urine sampling device and which houses the urinalysis device and the fluid pump, forms a single component part which is self-contained, it can be readily installed on the upper surface of the bowl fixture between the bowl and the flushing water supply section. The urinalysis unit of the invention may be readily mounted to an existing toilet by removing an existing toilet seat from the existing standard bowl fixture and by installing the housing in place of the existing toilet seat. Therefore, it is easy to reform an existing toilet having a standard bowl fixture into a toilet with a urinalysis function.

In a preferred embodiment, the urinalysis device includes a polarographic flow-cell and the fluid transfer device is adapted to transfer the urine sample to the flow cell by way of a carrier liquid. The polarographic flow-cell preferably includes a working electrode carrying an enzyme, such as glucose oxidase, that selectively promotes reaction of a predetermined constituent of urine. The flow cell issues an electric signal indicative of the amount of the urine constituent. Use of the flow cell having a working electrode supporting an enzyme is advantageous in reducing the cost of urinalysis because use of expensive liquid reagent is avoided. Furthermore, the maintenance of the unit is simplified since the storage and maintenance of reagent are not necessary. Additionally, the polarographic flow-cell is suitable to perform a high degree of quantitative analysis of urine. As the urine sample is transferred to the flow cell after being mixed with the carrier liquid, the activity of the enzyme is sustained for a long period so that the service life of the flow cell is prolonged.

Preferably, the polarographic flow-cell comprises a disposable flow-cell which is replaceably mounted to a support socket fixed to the housing. The flow cell and the support socket therefor are provided with mating faces extending perpendicular to the direction of mounting of the flow cell against the socket so that upon displacing the flow cell toward the socket in the direction of mounting, the flow cell and the socket are hydraulically and electrically connected with each other. It is preferable to provide a clamp mechanism to facilitate replacement of the flow cell.

The carrier liquid may be stored in a carrier liquid reservoir arranged in the housing. In a preferred embodiment, however, the carrier liquid reservoir is mounted to a toilet lid which is hinged to the housing. With this arrangement, a large capacity is provided for the storage of carrier liquid and the housing may be made compact. Furthermore, by mounting the carrier liquid reservoir to the toilet lid, the level of the carrier liquid in the reservoir is considerably elevated with respect to the fluid pump and the flow cell arranged in the housing. This advantageously precludes air bubbles from entering the carrier liquid being transferred to the flow cell whereby the accuracy of urinalysis is improved.

In a preferred embodiment, the fluid pump comprises an electrically driven syringe pump which is coupled to an electric valve preferably of the rotary type. The syringe pump and the rotary valve are preferably arranged substantially coaxially with each other so as to form a compact unitary module which may be readily arranged within the housing of the urinalysis unit. The rotary valve includes a first port in communication with the pumping chamber of the syringe pump, a second port in communication with the urine sampling vessel, a third port in communication with the carrier liquid reservoir, and a fourth port in communication with the flow cell, the rotary valve being arranged such that the first port is selectively connected with the second, third or fourth port. The syringe pump and the rotary valve concert together to draw the urine sample sampled by the sampling vessel into the pumping chamber of the syringe pump, to inject a metered quantity of urine sample toward the flow cell and to propel the thus injected urine sample to the flow cell by the carrier liquid.

As in this way the syringe pump cooperates with the rotary valve to achieve all the four functions of suction of urine sample, metering of urine sample, injection of urine sample into the carrier liquid, and transfer of the urine sample and carrier liquid toward the polarographic flow-cell, the number of components parts of the urinalysis unit can be minimized and the housing of the unit may be made small and compact. In response to the reduction in the number of component parts, the structure of the urinalysis unit as well as the assemblage of parts are simplified.

In an alternative embodiment, the third port of the rotary valve may be connected to a reservoir for a liquid reagent to ensure that the urine sample together with the reagent are drawn into the pumping chamber of the syringe pump and that the mixture of urine sample and reagent is transferred to the flow cell in a batch process.

Preferably, the urine sampling device comprises a swingable arm and an electrical drive therefor, with an end of the arm being supported by the toilet seat for pivoting movement about a horizontal axis, with the other end of the arm supporting the urine sampling vessel. The electrical drive is preferably operable to move the urine sampling vessel along the inner surface of the bowl between a rest position in which the sampling vessel is situated adjacent the frontal part of the rim of the bowl fixture and is substantially concealed underneath the toilet seat and an operative position in which the sampling vessel is situated within the inner space of the bowl in the vicinity of the bottom of the bowl.

As in this manner the sampling vessel is movable along the inner surface of the bowl from the rest position located close to the frontal part of the rim to the operative position located rearwardly and downwardly thereof, the sampling vessel can readily be displaced to follow the fall position of urine column whenever the trajectory of urine column is deflected in the fore-and-aft direction for any reason such as the sexual difference of the user. Accordingly, urine can be sampled readily and with certainty regardless of whether the user is male or female and even when the amount of urination is insufficient. Since the urine sampling vessel is moved along the inner surface of the bowl so that it does not interfere with the body of the user as seated on the toilet seat, the toilet is comfortable to use and any inadvertent damage that may occur on the movable parts of the electrical drive due to contact with the user's body is avoided.

Preferably, the urine sampling device includes a frame secured to the toilet seat at the underside thereof and supporting the swingable arm and the electrical drive. The frame is preferably arcuated to extend along the toilet seat in such a manner that it is substantially concealed by the toilet seat in the horizontal position of the toilet seat. It is preferable that the frame is confined within a vertical gap defined between the upper surface of the rim of the bowl and the lower surface of the toilet seat. With this arrangement, the toilet seat as incorporating the urine sampling device presents a simple outer configuration and gives an improved appearance. Additionally, a robust yet compact urine sampling device is realized while retaining the mechanical strength of the toilet seat.

Preferably, the urine sampling device is provided with cleansing device such as spray nozzle to cleanse the urine sampling vessel with water after use. With this arrangement, the urine sampling vessel is kept clean and fresh urine free from contamination can be sampled.

The toilet seat is preferably provided at the lower surface thereof with a downwardly directed concavity in which at least a part of the electrical drive is accommodated. This arrangement enables to increase the size of the electrical drive thereby to enhance the operational reliability thereof.

In another aspect, this invention provides a method for reforming an existing toilet having a standard water closet bowl fixture into a toilet with a urinalysis function. According to the invention, a toilet seat assembly incorporating a built-in urine sampling device is prepared. This seat assembly is preferably prefabricated by preparing a toilet seat provided at the lower surface thereof with a downwardly directed concavity and by mounting the frame to the underside of the seat in such a manner that at least a part of the electrical drive is accommodated in the concavity. When reforming the toilet, an existing standard toilet seat is removed from the existing bowl fixture and a housing is mounted on the upper surface of the bowl fixture between the bowl and the flushing water supply section. Prior to or subsequent to the step of mounting of the housing, the toilet seat assembly as a whole together with the urine sampling device incorporated therein is mounted to the housing and electrical and hydraulic connection are completed as required.

Use of the prefabricated toilet seat assembly having a built-in urine sampling device advantageously enables to determine initially the overall design of the toilet seat assembly in a totally integrated manner in anticipation that the urine sampling device is to be incorporated into the toilet seat. Thus, when designing the dimension and shape of the toilet seat assembly, it is possible to take the urine sampling device into account in such a manner that the mechanical strength of the assembly is retained. The assemblies may be prefabricated in a mass production process in a factory wherein a high degree of quality control is attained. Similarly, a concavity may be formed in advance on the underside of the toilet seat and the electrical drive for the swingable arm may be accommodated by making use of the concavity. As in this manner quality controlled production is available and the space within the toilet seat is effectively utilized in designing the urine sampling device, it is possible to realize a urine sampling arrangement which is robust and has an assured operational reliability and is capable of sampling urine without failure.

Reforming of the toilet can be simply and readily carried out since it suffices to replace the prefabricated toilet seat assembly for the existing toilet seat without requiring mechanical work to be made on the existing seat.

The present invention also provides a combined toilet lid and reservoir assembly suitable for use in the urinalysis unit. The combined assembly is comprised of a swingable toilet lid and a substantially flat carrier-liquid reservoir secured to the toilet lid. The reservoir is preferably provided with a mechanism for permitting inspection of the level of carrier liquid remaining therein.

These features and advantages of the invention, as well as other features and advantages thereof, will become apparent from the following description made with reference to the preferred embodiments thereof.

BEST MODE FOR CARRYING OUT THE INVENTION

Figure 1:
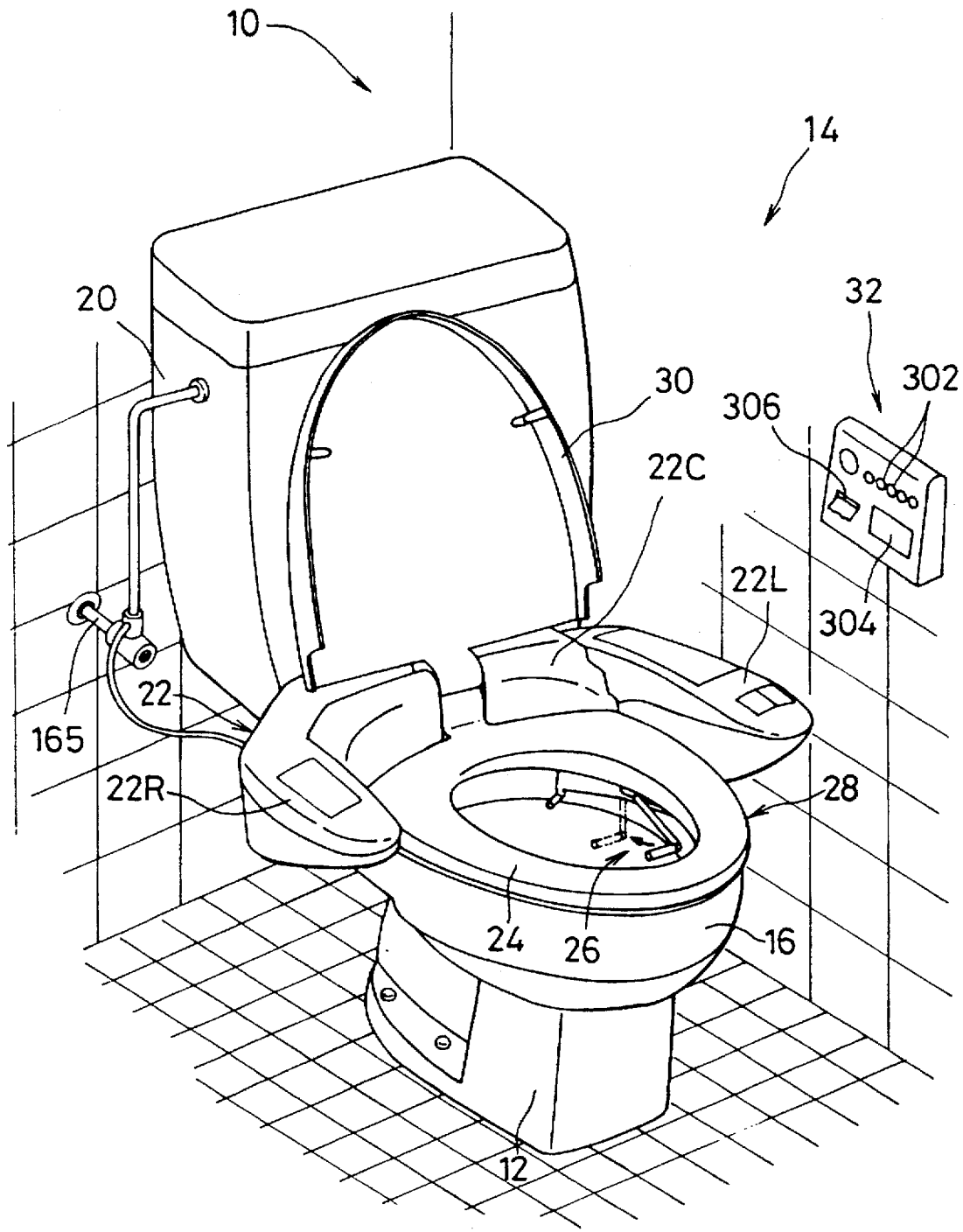
FIG. 1 is a perspective view showing the urinalysis unit of the invention as mounted to a standard water closet bowl fixture of toilet.
Figure 2:
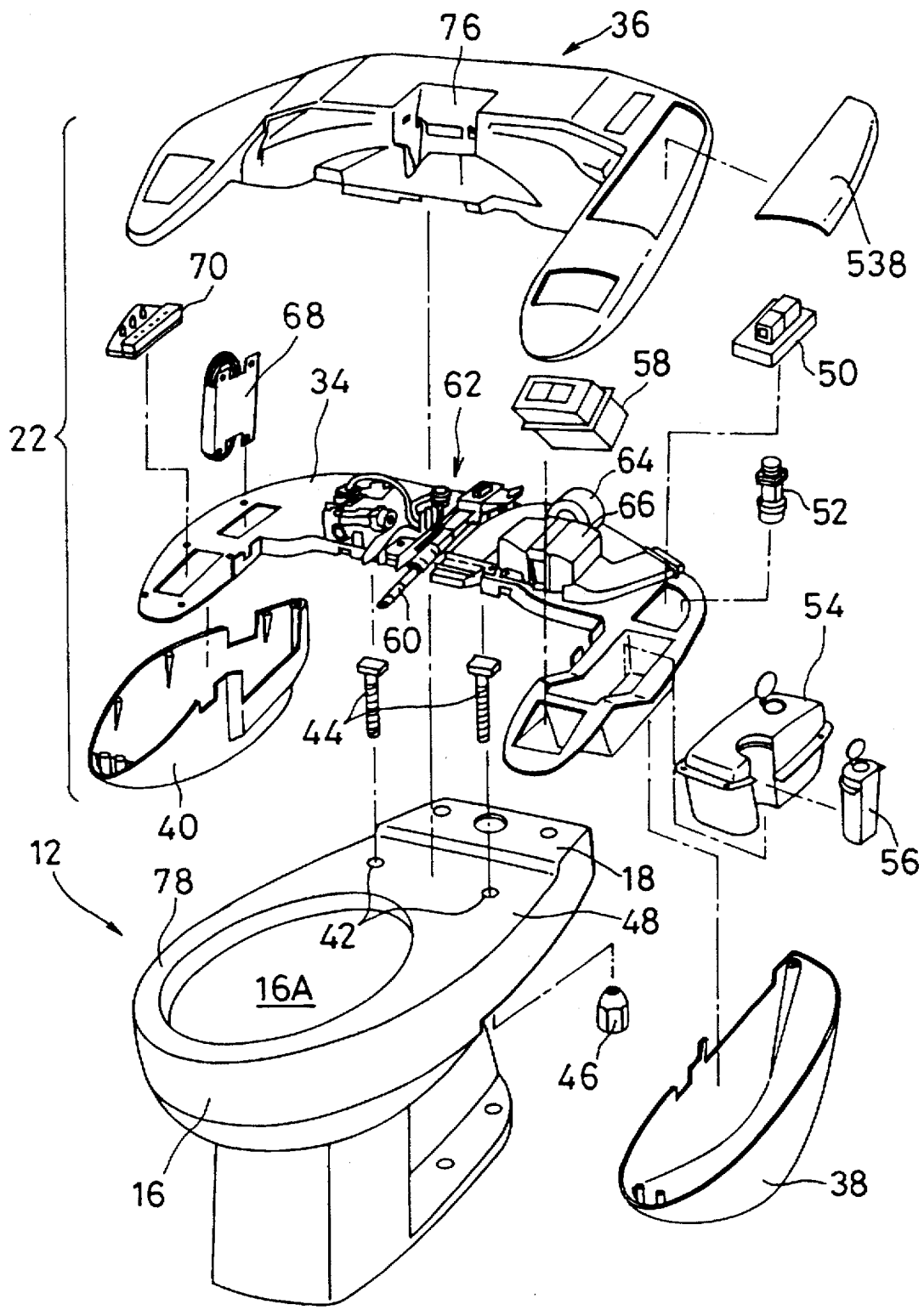
FIG. 2 is an exploded perspective view of the housing of the urinalysis unit illustrated in FIG. 1.
Figure 3:
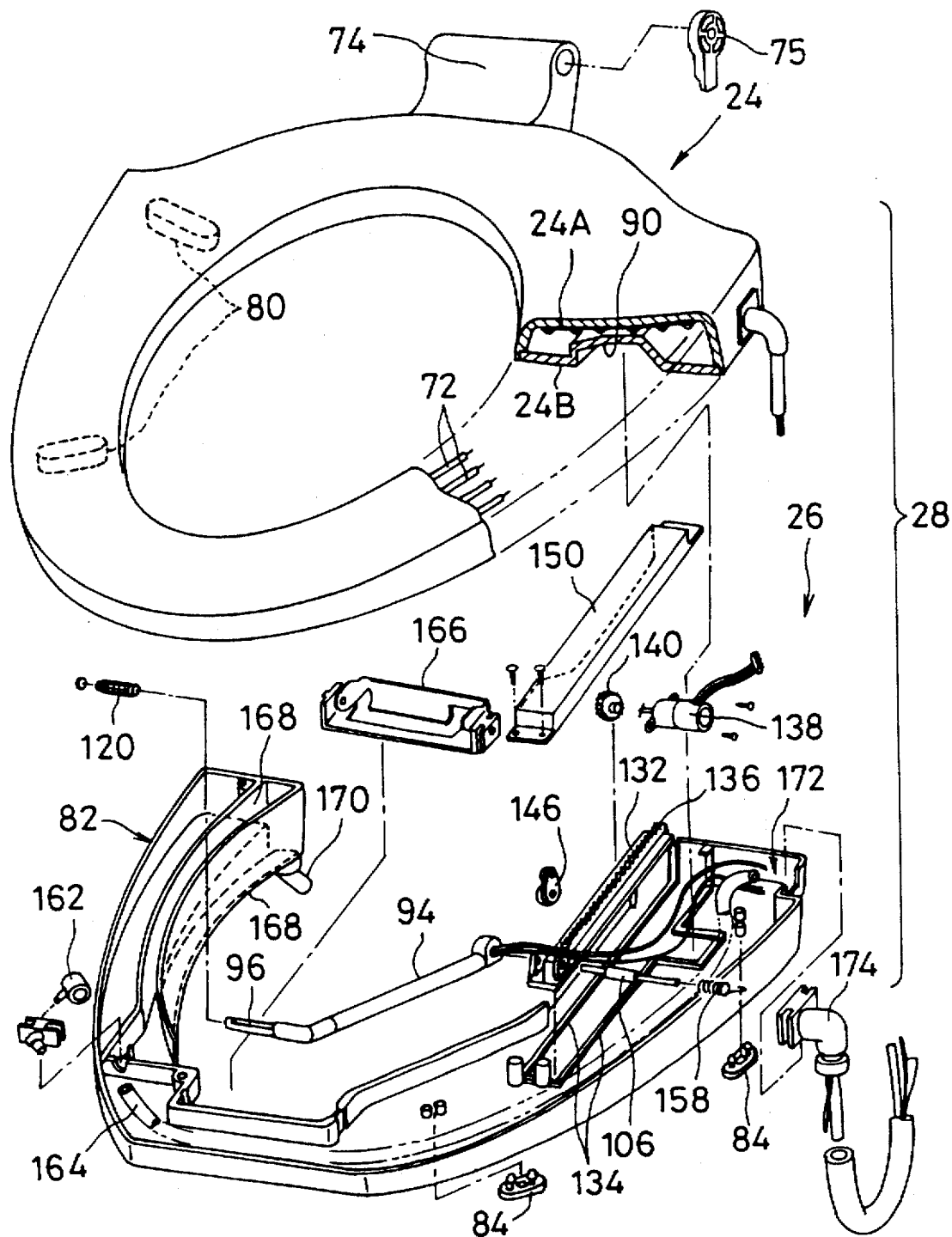
FIG. 3 is an exploded perspective view, partly cut away, of the toilet seat assembly of the urinalysis unit shown in FIG. 1.

Referring to FIGS. 1–3, the toilet 10 is provided with a standard water closet bowl fixture 12 which is installed on the toilet floor in the conventional manner. Mounted to the toilet bowl fixture 12 is a urinalysis unit 14 according to the invention. The urinalysis unit 14 of the invention may be mounted to any standardized toilet bowl fixture available on the market, including vortex type, siphon type, siphon jet type, and wash-down type. The standard bowl fixture is provided with a conventional bowl 16 and a flushing water supply section 18 located rearwardly of the bowl. In the illustrated embodiment, the flushing water supply section comprises a cistern mounting section 18 to which a conventional cistern 20 is mounted in a conventional manner. The urinalysis unit 14 according to the invention may equally be mounted to a standard bowl fixture of the type in which flushing water is supplied through a flushing pipe equipped with a flushing valve instead of a cistern.

The urinalysis unit 14 includes a housing 22 which is fixed to the bowl fixture 12 as described later and a toilet seat 24 which is pivotally hinged to the housing 22. The toilet seat 24 is provided with a urine sampling device 26 adapted to sample urine in mid air within the inner space 16A of the bowl, the sampling device being incorporated in the toilet seat to form a built-in toilet seat assembly 28 (referred-to hereinafter as "toilet seat assembly"). The toilet seat assembly 28 is preferably prefabricated by assembling the urine sampling device 26 to a specially made toilet seat 24. A conventional toilet lid 30 may also be hinged to the housing. A control unit 32 for controlling the urinalysis unit 14 and for outputting the results of urinalysis may be disposed on the side wall of the toilet.

As shown in FIG. 2, the housing 22 of the urinalysis unit 14 may comprise, for example, a frame 34, an upper casing 36 and a pair of lower casings 38 and 40. These component parts of the housing 22 may be formed by injection molding of plastics and may be fastened together by screws and the like to form an integral housing 22. As shown in FIG. 2, the conventional standard toilet bowl fixture 12 is generally provided, between the bowl 16 and the flushing water supply section 18, with a pair of seat mounting holes 42 for use in mounting the conventional toilet seat. The housing 22 of the urinalysis unit 14 is also secured to the bowl fixture 12 by making use of these holes 42. To this end, an existing toilet seat is removed from the bowl fixture 12 if it is already mounted thereto. Then the frame 34 of the housing 22 is fixed on the upper surface 48 of the bowl fixture 12 between the bowl 16 and the cistern mounting section 18 by engaging a pair of T-bolts 44 into a pair of T-shaped slots formed on the underside of the frame 34 as described in JP-Y-63-6291 and by inserting the T-bolts 44 through the seat mounting holes 42 followed by screwing associated nuts 46.

As best shown in FIG. 2, the frame 3 has a central portion extending transversely of the bowl fixture 12 and a pair of lateral portions extending forwardly from the ends of the central portion, the upper casing 36 being shaped to conform to the frame 14. Accordingly, the frame 34, the upper casing 36 and the lower casings 38 and 40 concert together to form the central portion 22C, left-hand lateral portion 22L and the right-hand lateral portion 22R of the housing 22 as shown in FIG. 1.

As shown in FIG. 2, within the left lateral portion 22L of the housing, there may be arranged a urinalysis device 50 for analyzing the urine sample sampled by the toilet seat assembly 28, an electrically driven syringe pump 52 for transferring urine sample and carrier liquid to the urinalysis device 50, a carrier liquid reservoir 54, and a reservoir 56 for calibration solution. Additionally, a digital sphygmomanometer unit 58 may be arranged on the left-hand portion 22L of the housing to enable the user to monitor the artery blood pressure by engaging the left second finger of the user. The digital sphygmomanometer unit 58 need not be described as it does not form part of the invention. In the illustrated embodiment, a conventional bidet system 62 having a spray nozzle 60 for producing an upwardly directed spray to wash the perineal part of the user, a conventional hot-air blower and drier unit 64, and a conventional deodorizer unit 66 with an ozonizer are arranged within the central portion 22C to provide additional functions when the toilet 10 with the urinalysis unit 14 is used for routine purposes. However, these additional functions are not indispensable for the purpose of the present invention and may therefore be omitted. A power source 68 for the urinalysis unit 14 and a control panel 70 for the bidet system may be stored within the right lateral portion 22R of the housing.

Referring primarily to FIGS. 3–8, the toilet seat assembly 28 comprised of the toilet seat 24 and the urine sampling device 26 incorporated therein will be described. In the illustrated embodiment, the toilet seat 24 is designed and manufactured in an attempt to incorporate the urine sampling device 26 therein and, accordingly, has a design suitable to meet with this purpose. As shown cut away in FIG. 3, the toilet seat 24 may be formed from an upper half 24A and a lower half 24B of impact resistive plastics which are joined together by high-frequency fusion bonding, with an electric heater wire 72 for heating the toilet seat being arranged as required. The seat 24 may be pivotally mounted to the housing 22 by a suitable hinge. Preferably, the seat 24 is mounted to the housing 22 by journaling the hinge portion 74 thereof by a retainer block 75 as described in Japanese Utility Model Application No. 5-19341 and by engaging the retainer block 75 within a bearing portion 76 (FIG. 2) of the housing 22.

In order to accommodate the toilet seat to any sintering distortion that may be developed in the bowl fixture 12 as a result of sintering process during the production thereof, the toilet seat 24 is preferably supported at four points against the upper surface of the rim 78 of the bowl fixture 12 in a manner similar to the conventional toilet seat. To this end, a pair of support legs 80 with cushioning pads may be provided in the conventional manner at the underside of the seat 24 as shown by dotted line in FIG. 3. At the other two points, the toilet seat 24 is supported by a pair of legs 84 mounted to a casing or frame 82, described later, of the urine sampling device. As will be understood from FIG. 8, due to the presence of the legs 80 or 84, an annular gap having a height of about 1.5–2 cm is left between the upper surface 86 of the rim 78 of the bowl fixture and the lower surface 88 of the seat 24. A part of the urine sampling device 26 is arranged and accommodated by making use of a part of the annular gap. As will be apparent from FIGS. 3 and 8, the toilet seat 24 is provided at the underside thereof with a pair of downwardly directed concavities 90 and 92 so as to accommodate part of the components of the urine sampling device 26 as described later.

The urine sampling device 26 is generally designed such that a quantity of urine released into the bowl 16 of the bowl fixture 12 is received in mid air in the inner space of the bowl by a urine sampling vessel and that after sampling the sampling vessel is returned to a storage position underneath the toilet seat and is automatically washed with water. An embodiment of the urine sampling device 26 will be described with reference to FIGS. 3–8. In the embodiment shown, the urine sampling device 26 includes a generally crank-shaped swing arm 94, an elongated urine sampling vessel 96 detachably mounted to the free end of the swing arm, an electrical drive 98 for driving the arm 94, and the frame 82 for the urine sampling section. The swing arm 94 may be formed by a central elbow 100, an end elbow 102, a pipe 104 connecting these elbows, and a spindle 106, as shown in FIGS. 5 and 7.

Figure 6:
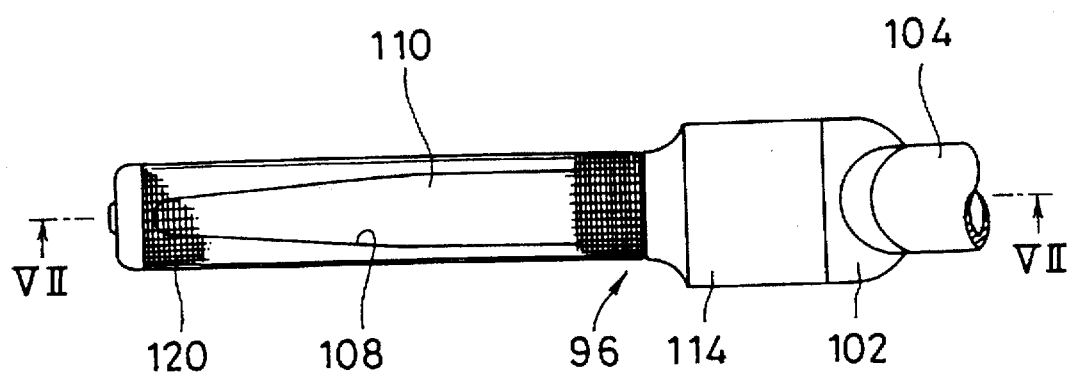
FIG. 6 is a top plan view of the urine sampling vessel mounted to the swing arm.
Figure 7:
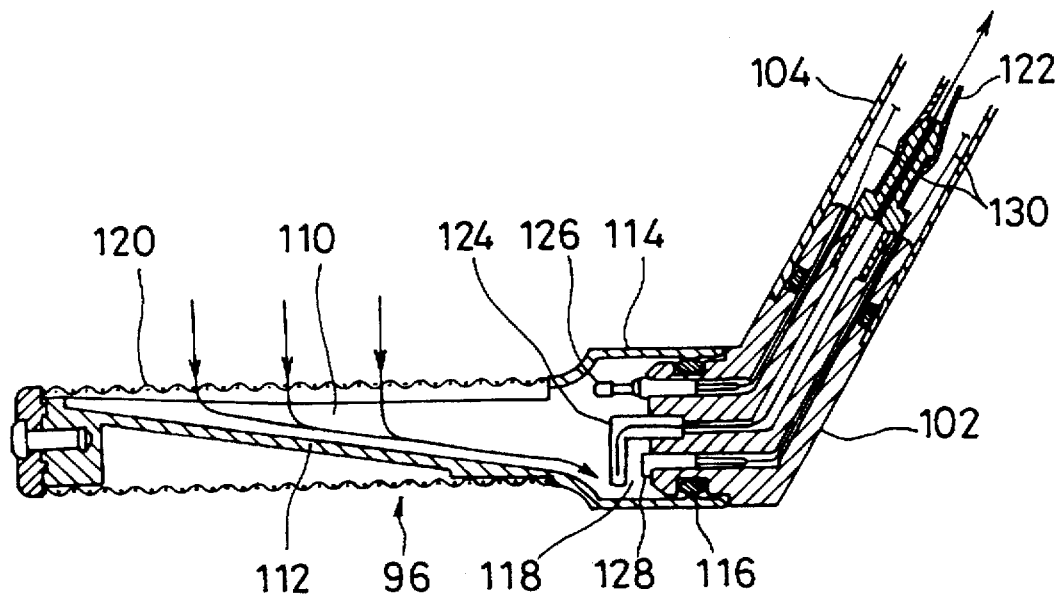
FIG. 7 is a cross-sectional view taken along the line VII—VII of FIG. 6.

As shown in FIGS. 6 and 7, the urine sampling vessel 96 may be comprised of a main body 112 having an elongated upper opening 108 and a trough-shaped cavity 110 and of a base 114 having an enlarged diameter, the urine sampling vessel 96 being detachably and liquid tightly mounted to the end elbow 102 by means of an O-ring 116. The cavity 110 formed in the main body is inclined toward the base 114 to ensure that urine fallen down into the cavity 110 is accumulated within a urine pool 118 defined by the base 114 and the elbow 102. Preferably, the outer periphery of the main body 112 is covered by a metal screen 120 to prevent urine excreted by the user and impinging on the urine sampling vessel 96 from splashing backwards and to effectively collect urine sample. Urine accumulated in the urine pool 118 is forwarded via a flexible tube 122 extending through an inner passage of the elbow 102 as well as through the swing arm 94 and its spindle 106 to the urinalysis device 50 located in the housing 22 under the action of the syringe pump 52 operating on its suction and delivery strokes. In order to exclusively pick up urine not containing air bubbles and to deliver it to the urinalysis device, the elbow 102 is preferably provided with an L-shaped suction pipe 124 which is open toward the bottom of the urine pool 118. A pair of vertically spaced electrodes 126 and 128 may be provided on the elbow 102 to detect whether a sufficient amount of urine has accumulated within the urine pool 118. These electrodes may be connected via lead wires 130 to a control circuit of the urinalysis device 50 arranged in the lateral housing 22L.

Figure 8:
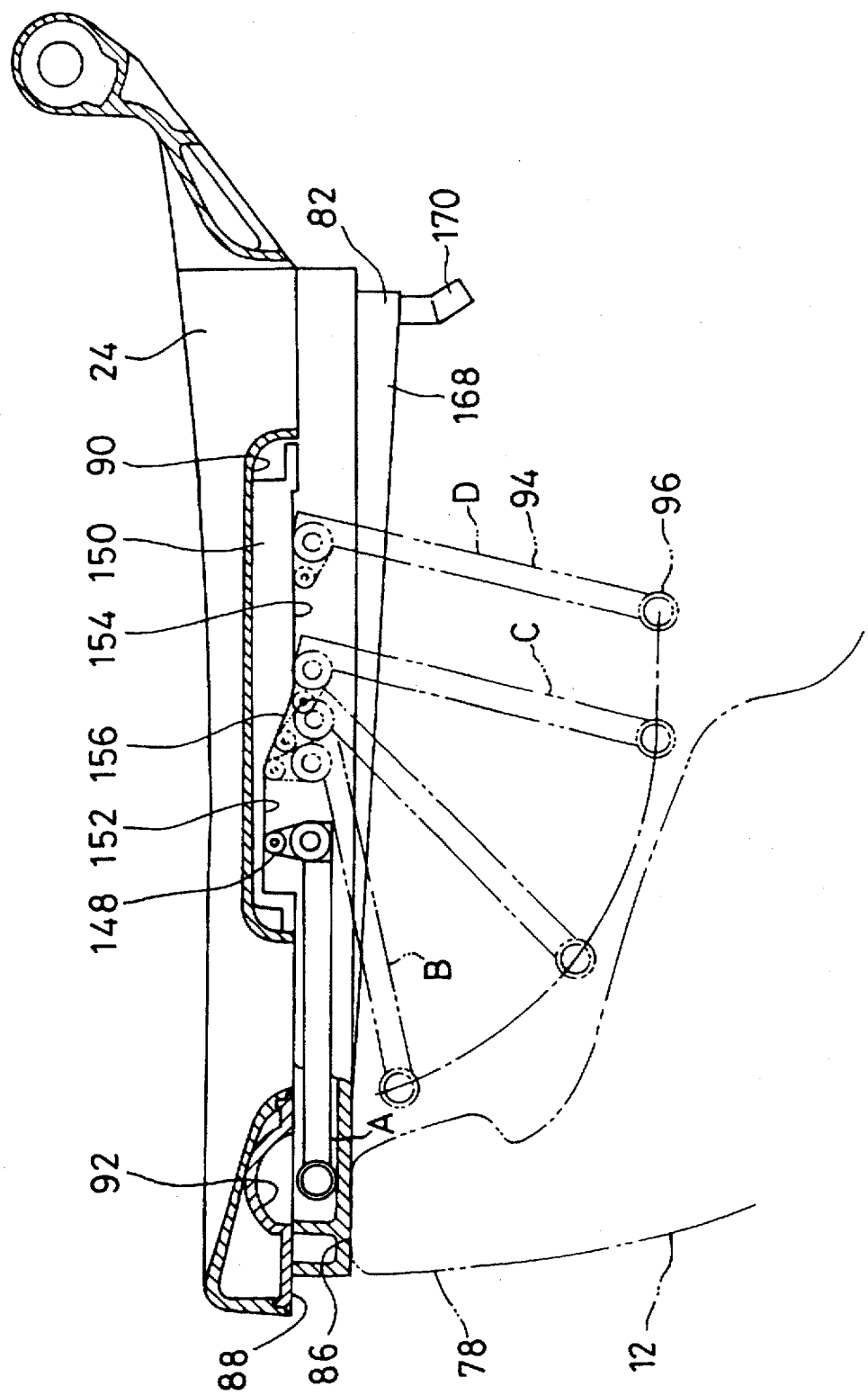
FIG. 8 is a schematic cross-sectional view taken along the line VIII—VIII of FIG. 4 and showing the swing arm and the urine sampling vessel in various different positions.

Generally, in the illustrated embodiment, the drive 98 for the swing arm 94 is adapted to impart a rotational movement as well as a translational movement to the swing arm 94 so as to move the urine sampling vessel 96 from the storage position situated underneath the frontal part of the toilet seat to various urine sampling positions, and vice versa, as best shown in FIG. 8.

Figure 4:
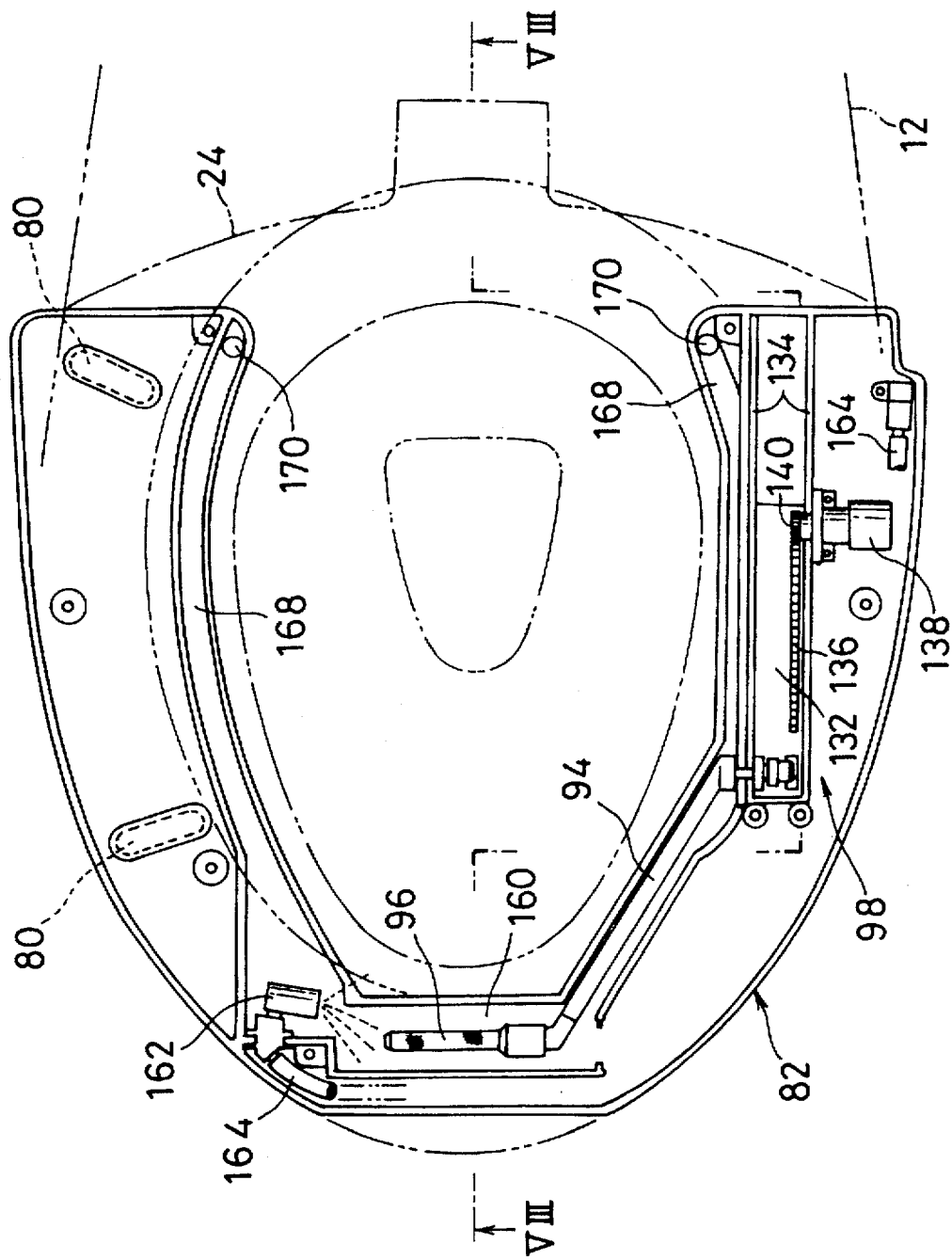
FIG. 4 is a plan view of the urine sampling device of the toilet seat assembly shown in FIG. 3, with the toilet seat, a cam plate and a swingable cover being removed and with the toilet seat and the toilet bowl fixture being shown by the phantom line and the dotted line, respectively.
Figure 5:
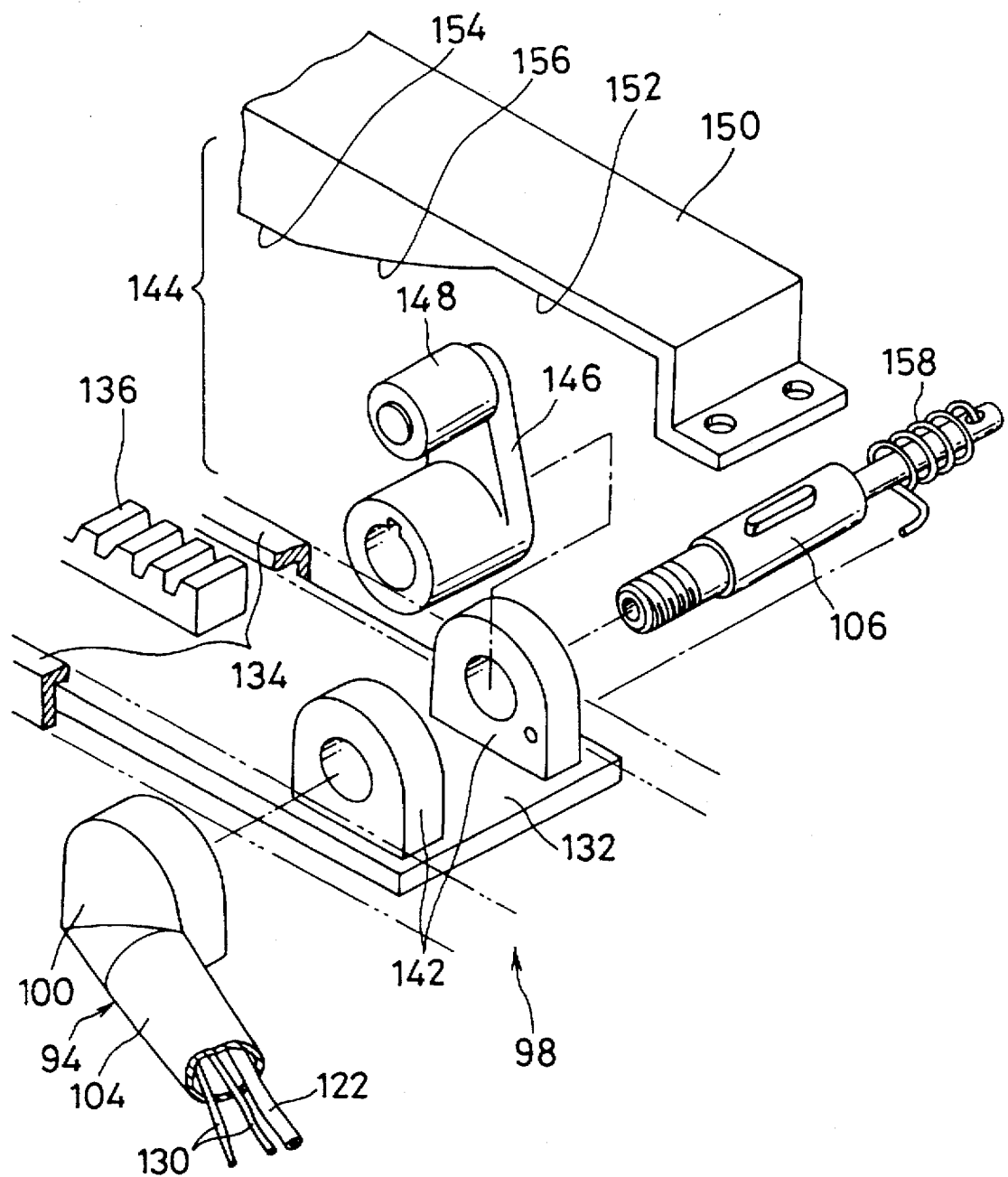
FIG. 5 is an enlarged exploded perspective view, partly cut away, of a part of the swing arm drive.

More specifically, referring to FIGS. 3–5, the drive 98 is arranged on the frame 82 suitably fixed to the underside of the toilet seat 24 by screws, for example. The drive 98 includes a slider 132 slidably mounted to the frame 82, the slider being guided for sliding movement substantially parallel to the longitudinal axis of the bowl fixture 12 by a pair of guide rails 134 secured to the frame 82. Secured to the slider 132 is a rack 136 with which is engaged a pinion 140 mounted to the output shaft of a stepping motor 138 provided with a reduction gear mechanism and fixed to the frame 82. Accordingly, rotation of the motor 138 in either direction will cause back-and-forth translational movement of the slider 132. The motor 138 is controlled by the control circuit, described later, received in the lateral housing 22L.

The swing arm 94 is rotatably journaled to the slider 132 and is supported by the slider for sliding movement conjointly therewith. To this end, the slider 132 is provided with a pair of trunnion bearings 142 as shown in FIG. 5 to rotatably support the spindle 106 of the swing arm 94. The spindle 106 has an axial bore through which the flexible tube 122 and the lead wires 130 are extended.

The drive 98 is further provided with a lever and cam mechanism 144 that controls the angular position of the swing arm 94 in such a manner that the angular position of the urine sampling vessel 96 is in turn controlled in response to the back-and-forth movement of the slider 132 caused by rotation of the motor 138. As best shown in FIG. 5, a lever 146 is mounted over the spindle 106 of the swing arm 94 between the bearings 142 for rotation integrally with the spindle and a cam follower 148 in the form of a roller is supported at the end of the lever 146. The cam follower 148 is adapted to cooperate with a cam plate 150 suitably secured to the frame 82 by screws and the like, the cam plate 150 being formed with a pair of staggered horizontal cam surfaces 152 and 154 and an inclined cam surface 156. An end of a coiled return spring 158 is fixed to the spindle 106 of the swing arm 94, the other end thereof being engaged with the bearing 142. The return spring 158 is preloaded such that the swing arm 94 is biased in the clockwise direction as viewed in FIG. 8.

The frame 82 carrying the swing arm 94 and the associated drive 98 of the urine sampling device 26 is rigidly secured to the toilet seat 24 by screws and the like to form the integral toilet seat assembly 28 incorporating the urine sampling device. As the toilet seat 24 is formed on the underside thereof with the prefabricated concavity 90 that corresponds in shape to the drive 98 as shown in FIGS. 3 and 8, the component parts of the drive 98 such as the motor 138, the pinion 140, the cam plate 150, the lever 146 and the cam follower 148 are accommodated partly in this concavity 90. Due to use of the toilet seat 24 which is specially designed in this manner to incorporate the urine sampling device 26 by effectively utilizing the space available in the toilet seat 24 to accommodate the component parts of the urine sampling device 26, it is possible to implement these component parts in a robust design. The specially-made toilet seat 24 may be manufactured on a mass production basis by using injection molds and the toilet seat assembly 28 may be prefabricated by incorporating therein the urine sampling device 26. When converting an existing toilet equipped with a standard bowl fixture into a toilet with the urinalysis function, the toilet seat assembly 28 may be mounted to the housing 22 at an appropriate timing prior to or subsequent to mounting of the housing 22 to the bowl fixture 12.

Referring primarily to FIG. 8, the operation of the urine sampling device 26 will be described. When the urine sampling device 26 is not in use, the slider 132 is in the forward-most position so that the cam follower 148 is engaged with the first horizontal cam surface 152 of the cam plate 150. As a result, the swing arm 94 is swung up under the action of the return spring 158 so that the urine sampling vessel 96 is held underneath the toilet seat 24 in the rest or storage position (position A) situated within the frame 82. With the urine sampling vessel in this position, the toilet seat assembly 28 may be swung up or down whenever the toilet is to be used for the purposes of routine excretion.

When the user is seated on the toilet seat 24 for the purposes of sampling and analysis of urine and turns on a start switch of the control unit 32, the motor 138 is rotated causing the rack and pinion mechanism 140/136 to commence the retracting movement of the slider 132 whereby the urine sampling vessel 96 is first pulled out horizontally and rearwardly from the storage position. As the cam follower 148 engages the inclined cam surface 156 of the cam plate 150, the lever 146 starts to rotate the swing arm 94 (position B). As the cam follower 148 rides further on the inclined cam surface 156, the swing arm is moved backward while being rotated thereby causing the urine sampling vessel 96 to displace along the arcuate path as shown in FIG. 8. As the motor 138 rotates further, the cam follower 148 comes to engage the second horizontal cam surface 154 of the cam plate 150 (position C), whereupon the swing arm 94 commences translational movement while retaining its angular position until it is brought to the rear extremity position D. It will be noted that, generally, the direction of urination is subject to fluctuation depending on the difference in the sexuality of the user so that in the case of a male the urine column tends to fall relatively forwardly in contrast to a female whose urine column tends to fall rearwardly. In addition, the direction of urination varies from individual to individual. Accordingly, it is preferable that the control switches for the motor 138 as well as the control circuit be arranged and designed such that, in the case of a male, the urine sampling vessel 96 is automatically brought to a predetermined position between the positions B–C, whereas in the case of a female, the urine sampling vessel 96 is automatically brought to a predetermined position between the positions C–D, as well as in such a manner that the user is permitted to finely adjust the position of the urine sampling vessel. The user may commence urination toward the urine sampling vessel 96 as it is brought to an appropriate position.

Urine impinged upon the urine sampling vessel 96 will flow down along the trough-shaped cavity 110 to accumulate in the urine pool 118. Urine thus sampled is sucked by the syringe pump 52 in the housing 22 via the L-shaped suction pipe 124 and the flexible tube 122 and is transferred to the urinalysis device 50 for quantitative analysis. Suction of the urine sample may be commenced automatically when, based on the signal from the electrodes 126 and 128, it is detected that urine has accumulated in the urine pool 118 up to the level of the upper electrode 128.

Upon completion of sampling and transfer of urine to the urinalysis device, the motor 138 is rotated in a direction to move the slider 132 forward whereby the urine sampling vessel 96 is returned to the position B in response to advancement and upward rotation of the swing arm 94 and is thereafter returned to the storage position A in response to the translational movement of the swing arm. The urine sampling vessel 96 stands by in this position. As the urine sampling vessel 96 is designed in an elongated form, it can be readily stored in a narrow space defined between the lower surface 88 of the toilet seat 24 and the upper surface 86 of the rim 78 of the toilet bowl fixture as shown in FIG. 8.

It is desirable that after urine sampling, the urine sampling vessel 96 soiled by urine be washed with water. To this end, it is preferable to form a storage and washing chamber 160 in the frame 82 and to arrange a spray nozzle 162 directed toward the washing chamber 160 as shown in FIGS. 3 and 4. The spray nozzle 162 may be connected through a hose 164 and a solenoid valve, described later, to a water line 165 (FIG. 1) to supply water under pressure. Alternatively, the hose 164 may be connected to a water supply valve of the bidet system 62. As shown in FIG. 3, the frame 82 may be provided with a swingable cover 166 to close the washing chamber 160 during washing so as to prevent splash of cleansing water. The swingable cover 166 may be interlocked by a suitable link, not shown, to the lever and cam mechanism 144 in such a manner that the cover 166 is open as the urine sampling vessel 96 is moved to and away from the washing chamber 160 and that the cover 166 is closed as the urine sampling vessel 96 is returned to the storage position in the washing chamber. As best shown in FIG. 8, the toilet seat 24 is provided with a concavity 92 accommodating the swingable cover 166 to permit the swingable cover 166 to rotate by making use of a space within the concavity 92. It will be noted that the provision for such concavity 92 is possible inasmuch as the toilet seat 24 is specially designed and fabricated.

Used washing water is preferably discharged into the toilet bowl 16. To this end, the frame 82 is provided with a pair of drainage troughs 168 extending rearwardly from the washing chamber 160 along the sides of the rim 78, as shown in FIGS. 3 and 4. These drainage troughs 168 are inclined rearwardly and downwardly as best shown in FIG. 8 and are communicated at the rear ends with slanted drainage pipes 170 mounted to the frame 82. Accordingly, when the toilet seat assembly 28 is in the horizontal position, water ejected from the spray nozzle 162 will flow rearwards along the inclined drainage troughs 168 and will be discharged into the bowl 16 through the drainage pipes 170. As the drainage pipes 170 are inclined, any droplets of residual water remaining in the troughs 168 will be drained through the drainage pipes 170 into the bowl 16 when the seat assembly 28 is swung up.

As shown in FIG. 3, the frame 82 is provided at its rear end with a recess 172 in which an adapter or grommet 174 is fitted, the flexible tube 122 and the lead wires extending from the swing arm 94 as well as the water hose 164 being arranged to extend through the adapter. Due to the presence of the adapter 174, the arrangement of the piping and wiring between the urine sampling device 26 and the housing 22 is simplified and any damages that would otherwise occur on the piping and wiring during swinging of the toilet seat assembly 28 is avoided.

Figure 9:
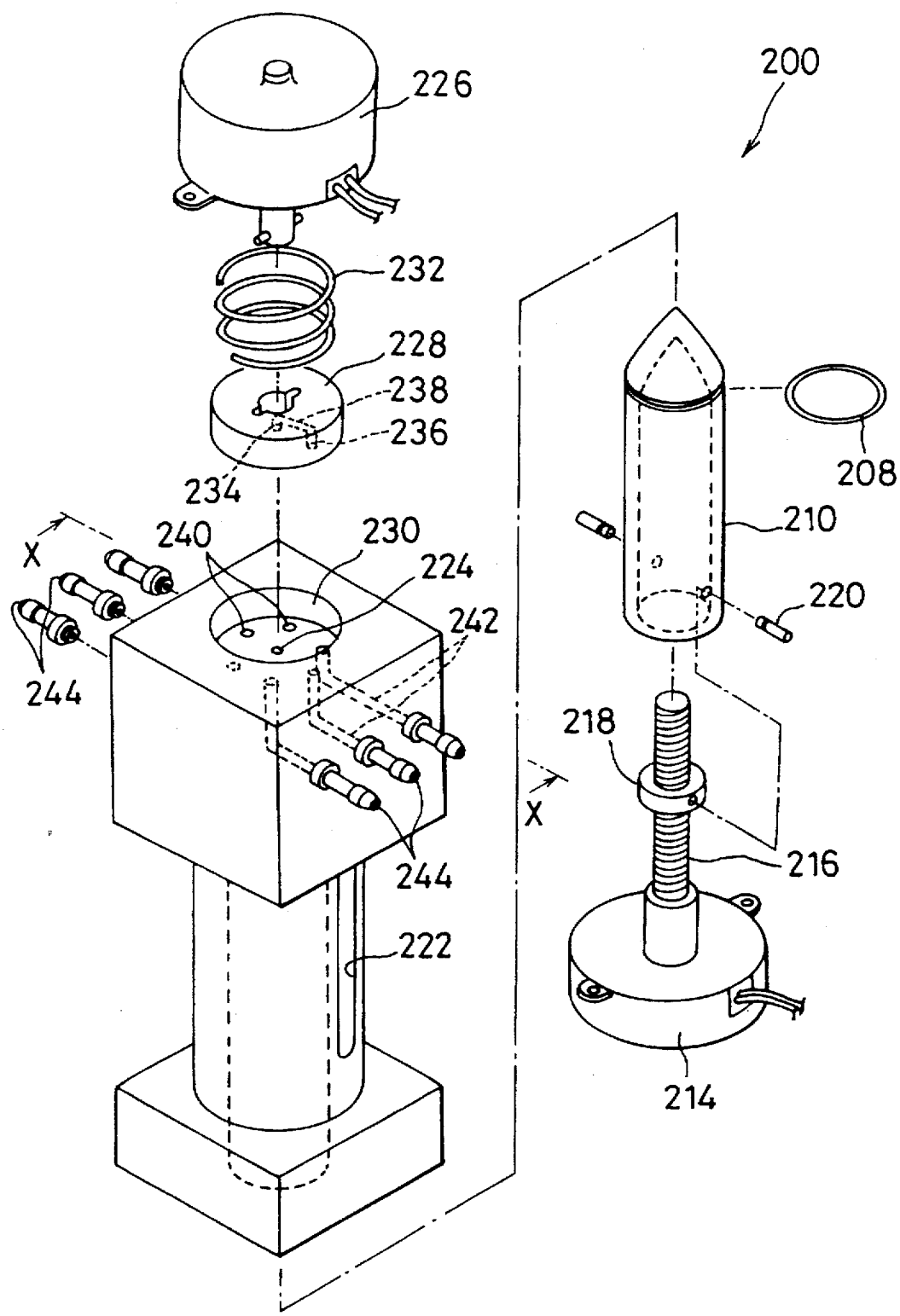
FIG. 9 is an exploded perspective view of a syringe pump, with a rotary valve, of the urinalysis unit shown in FIG. 1.
Figure 10:
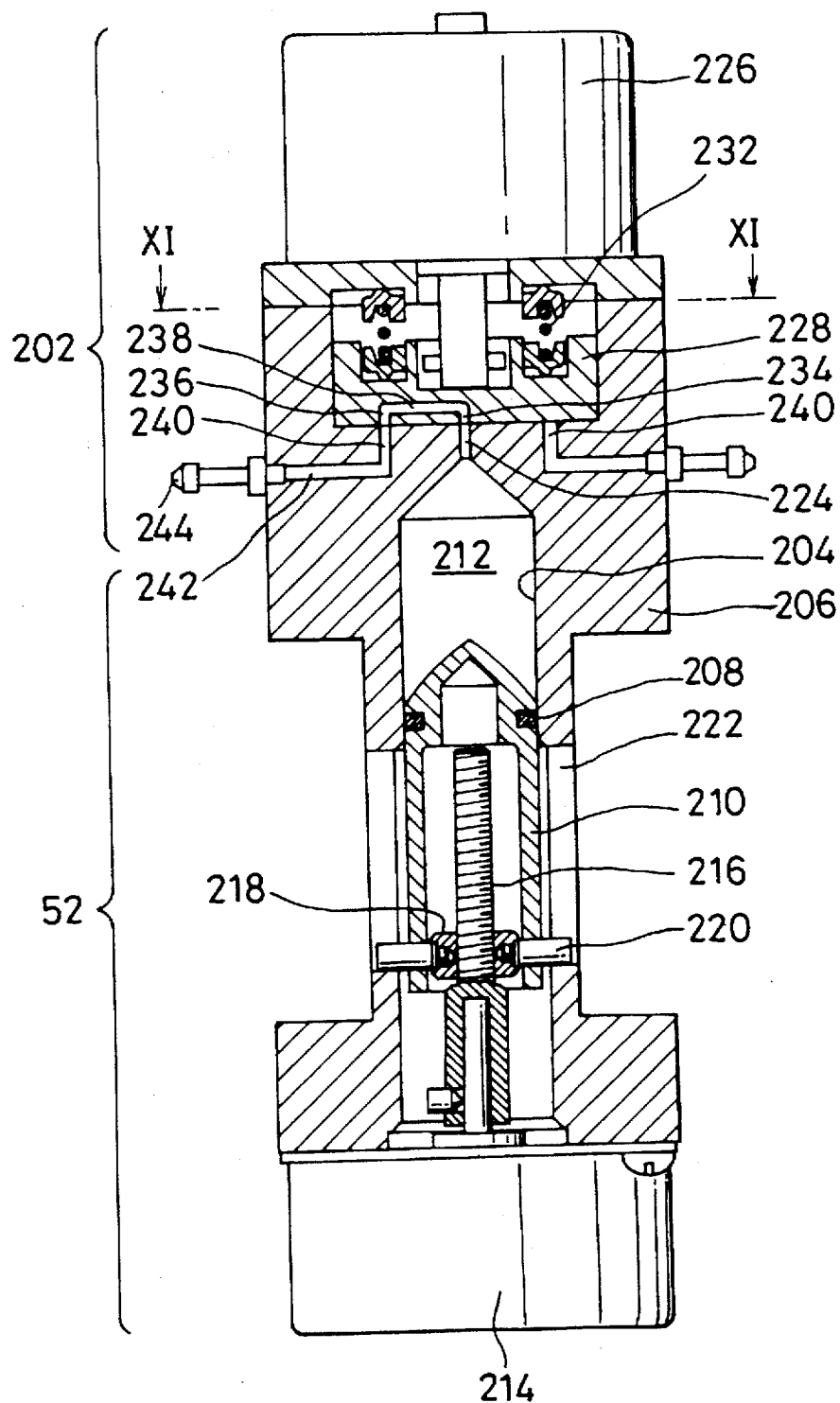
FIG. 10 is a cross-sectional view taken along the line X—X of FIG. 9.
Figure 11:
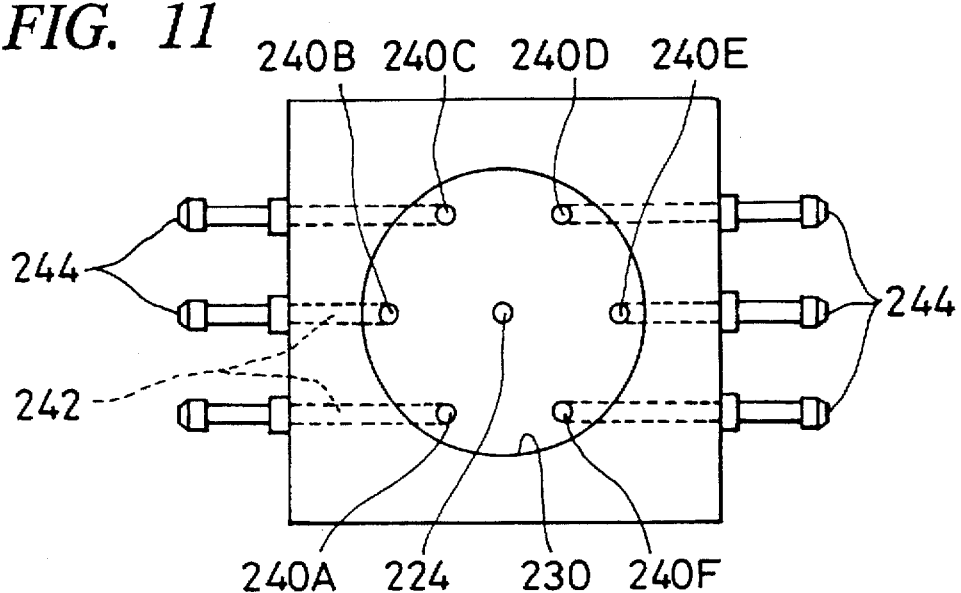
FIG. 11 is a cross-sectional view taken along the line XI—XI of FIG. 10, with a rotor removed.

Referring next to FIGS. 9–11, an embodiment of the electrically driven syringe pump 52 will be described. In the embodiment shown, the syringe pump 52 is designed to form essential part of the transfer system for transferring urine sampled by the urine sampling device 26 to the urinalysis device 50 and is also adapted to perform various other functions, described later, necessary for urinalysis. It will also be noted that in the illustrated embodiment the syringe pump 52 is provided with an electrically driven rotary valve 202 integrally incorporated therein to form a unitary module 200. However, the syringe pump 52 and the rotary valve 202 may be made separately and can be coupled with one another.

The syringe pump 52 has a main body 206 provided with a cylinder bore 204 in which a piston 210 with a sealing ring 208 is slidably fitted to form a pumping chamber 212 of variable volume. The piston 210 is reciprocated by a stepping motor 214 having an output shaft connected to a lead screw 216 with which a nut 218 is threadingly engaged. The piston 210 has a skirt across which a pair of diametrically opposed guide pins 220 are extended, the inner ends of these pins 220 being screwed into the nut 218. The guide pins 220 are respectively engaged within a pair of axial slots 222 formed in the main body 206. Accordingly, rotation of the motor 214 in one or other direction will cause the piston 210 to move downwards or upwards together with the nut 218 so that liquid will be pumped into or out of the pumping chamber 212. The pumping chamber 212 is in communication with a central port 224 through which liquid enters and leaves the rotary valve 202. In order to ensure that the rotation of the motor 214 is smoothly converted into the reciprocating motion of the piston 210 despite the presence of any misalignment of the axis of the piston 210 with respect to the axis of the lead screw 216, the nut 218 is preferably coupled to the piston 210 by means of a ball joint as disclosed in Japanese Patent Application No. 6-87400 filed Mar. 31, 1994.

The rotary valve 202 includes a disc-shaped rotor 228 which is rotated by a stepping motor 226 with a reduction gear mechanism and which is rotatably and closely fitted within a cylindrical recess 230 formed in the head of the module 200. The lower surface of the rotor 228 as well as the bottom surface of the recess 230 are precision machined to provide flat surfaces and the rotor 228 is urged by a coil spring 232 against the bottom surface of the recess 230 so that the lower surface of the rotor 228 is brought into liquid-tight contact with the bottom surface of the recess 230. The rotor 228 is provided with a central port 234 opposite to and aligned with the central port 224 of the syringe pump 52 and is also provided with an outer port 236 which is offset radially outwardly from the central port 234, the ports 234 and 236 being communicated with each other by a horizontally-extending internal passage 238.

Open onto the bottom surface of the recess 230 are 6 ports 240A–240F, for example, which are circumferentially equally spaced apart from each other and which are offset at the same radial distance as the outer port 236 of the rotor 228, the ports 240A–240F being in communication with associated nipples 244 A–244F, respectively, through corresponding inner passages 242 A–242F formed in the head of the module. As described later with reference to FIG. 18, these nipples 244 A–244F are connected respectively to hoses and conduits extending from the associated components of the urinalysis unit 14.

With the rotary valve 202 of such arrangement, when the motor 226 is driven to rotate the rotor 228 until the outer port 236 of the rotor 228 is aligned with either one of the ports 240 A–240F, the pumping chamber 212 of the syringe pump 52 will be connected to the associated one of the nipples 244 A–244F. As the syringe pump 52 is actuated with the rotary valve in this position, liquid will be drawn from or delivered toward the selected one of the ports 240A–240F.

Referring next to FIGS. 12–16, an embodiment of the urinalysis device 50 of the urinalysis unit 14 will be described. In the illustrated embodiment, the urinalysis device 50 is designed to perform quantitative analysis of urinal glucose contained in the urine sample by way of the polarographic process. However, in lieu of the polarographic device, the urinalysis unit 14 according to the invention may be comprised of other type of urinalysis device wherein urinalysis is carried out by way of liquid chromatographic process or colorimetric analysis process. Furthermore, urinalysis device suitable to analyze protein, occult blood and other urinal substances may be provided in addition to the polarographic device adapted for glucose analysis.

Figure 12:
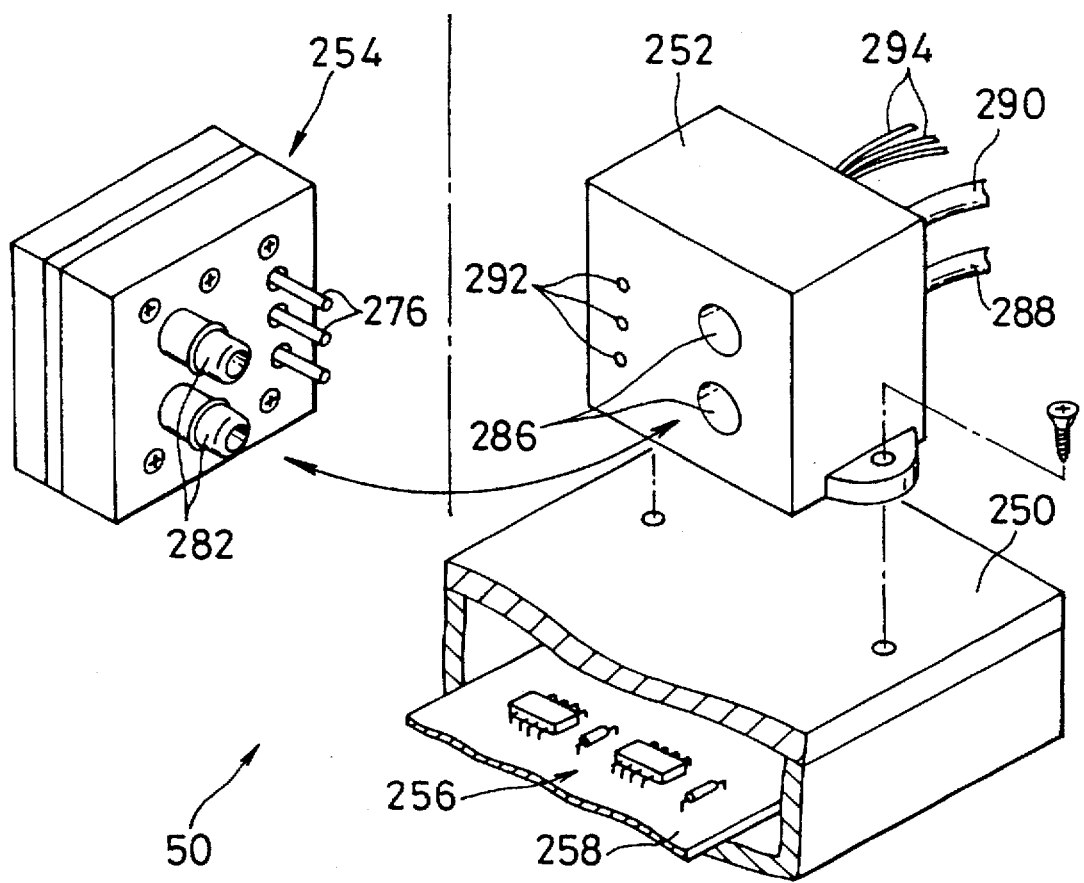
FIG. 12 is an exploded perspective view, partly cut away, of the urinalysis device of the urinalysis unit shown in FIG. 1.

As shown in FIG. 12, the urinalysis device 50 may comprise a base plate 250 adapted to be fixed to the frame 34 of the housing 22, a socket member 252 suitably secured to the base plate 250 by screws and the like, and a polarographic flow cell 254 detachably and replaceably mounted to the socket member 252, with a circuit board 258 carrying a control circuit 256 for the urinalysis unit 14 being arranged on the reverse side of the base plate 150.

Figure 13:
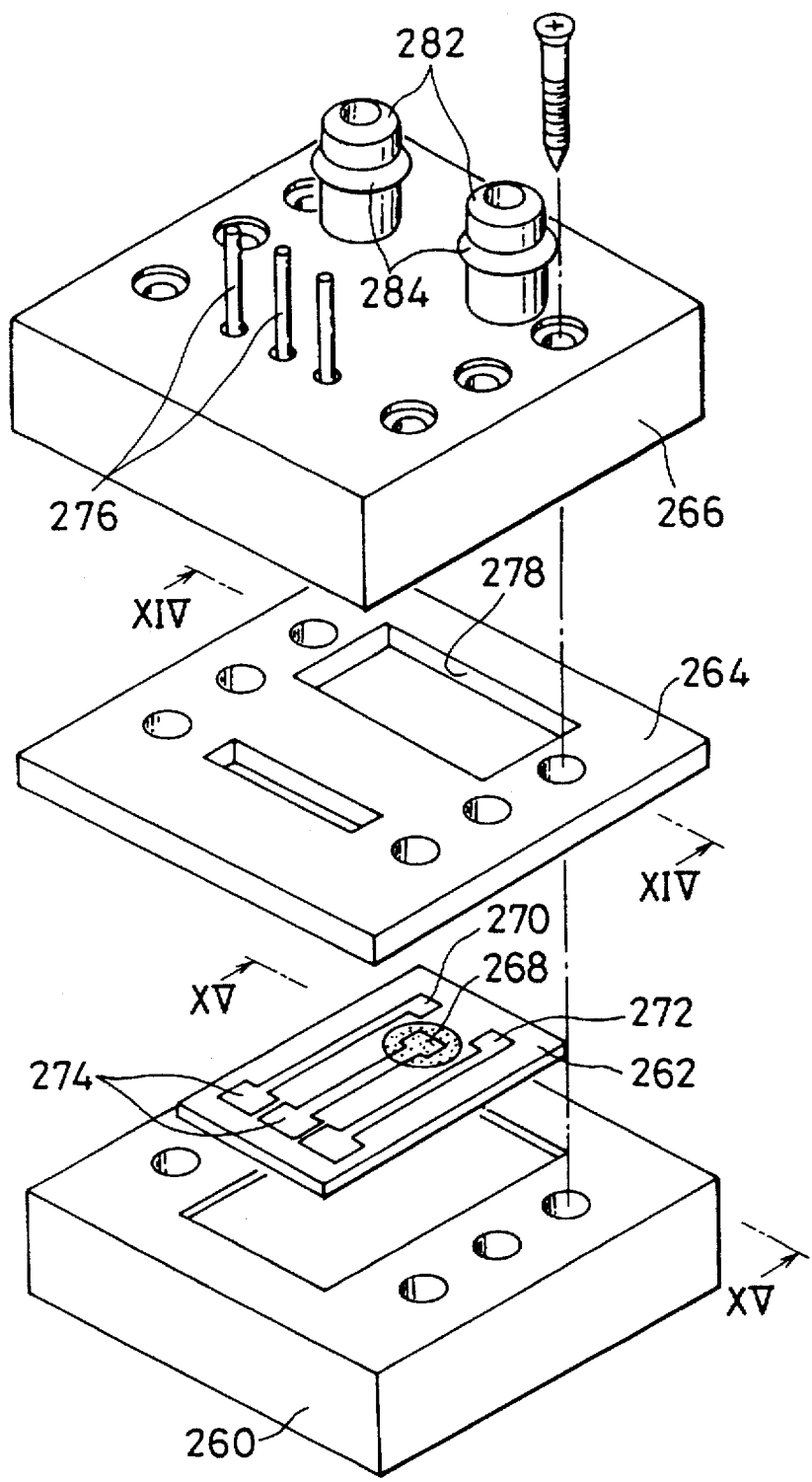
FIG. 13 is an enlarged exploded perspective view of the polarographic flow-cell shown in FIG. 12.
Figure 14:
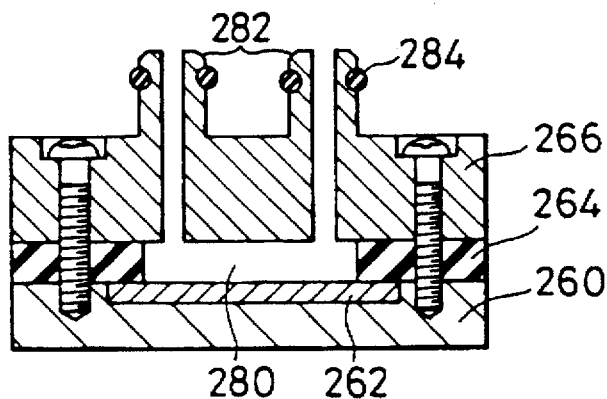
FIG. 14 is an enlarged cross-sectional view of the flow cell taken along the line XIV—XIV of FIG. 13.

As will be apparent from the exploded view shown in FIG. 13, the polarographic flow cell 254 may be comprised, for example, of a plastic base 260, a ceramic substrate 262 carrying electrodes, a spacer 264 of silicone rubber, and an upper plate 266 of plastics, these members being held together liquid-tightly by means such as screws. The ceramic substrate 262 may be made from alumina ceramics and is provided with a working electrode 268 of platinum, a counter electrode 270 of platinum and a reference electrode 272 of silver coated with silver chloride, the electrodes being formed by printing of metallic paste followed by firing. The electrodes are provided with respective terminals 274 with which connecting pins 276 mounted on the upper plate 266 are brought into contact, respectively. At the region facing the electrodes, the spacer 264 is recessed by an opening 278 thereby to form an electrolytic chamber 280 as shown in FIG. 14. The upper plate 266 is provided with a pair of nipples 282 in communication with the electrolytic chamber 280 so as to supply urine sample and carrier liquid to the electrolytic chamber. O-rings 284 are fitted over the outer periphery of the nipples 282 to ensure that, when the polarographic flow cell 254 is mounted to the socket member 252, the nipples 282 are liquid-tightly engaged within connection bores 286 in the socket member 252 to permit urine sample and carrier liquid to flow across the electrolytic chamber 280 through transfer tubes 288 and 290. The socket member 252 is also provided with pin receptacle holes 292 for engagement by pins 276 to establish the electrical connection between three electrodes 268, 270 and 272 and associated lead wires 294.

Figure 15:
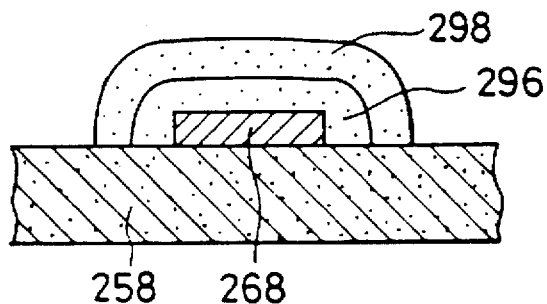
FIG. 15 is an enlarged schematic cross-sectional view of a working electrode taken along the line XV—XV of FIG. 13.

As schematically shown in FIG. 15, the platinum working electrode 268 is coated in sequence with a permselective membrane 296 made of a substance such as albumin and cellulose acetate that selectively permits permeation of hydrogen peroxide and with an enzyme fixed membrane 298 containing glucose oxidase (GOD). The GOD fixed membrane 298 may be formed by preparing an aqueous solution containing 4 parts by weight of GOD (for example, G7141 marketed by Sigma Corp.) and 1 part by weight of albumin, by dropping the solution on the permselective membrane 296 and by exposing the product to an aldehyde atmosphere for about 30 minutes. As glucose contained in the urine sample within the electrolytic chamber 280 is brought into contact with the GOD fixed membrane, GOD oxidizes glucose ($C_6H_{12}O_6$) to produce gluconic lactone ($C_6H_{10}O_6$) and hydrogen peroxide ($H_2O_2$) as follows.

(1)

As $H_2O_2$ thus produced passes across the permselective membrane 296 to reach the platinum working electrode 268, $H_2O_2$ is disintegrated into water and oxygen under the catalytic action of platinum upon donating electron to the working electrode 268. Due to the presence of the permselective membrane 296, any interfering substances having a molecular weight greater than that of $H_2O_2$ are precluded from reaching the working electrode 268.

Figure 16:
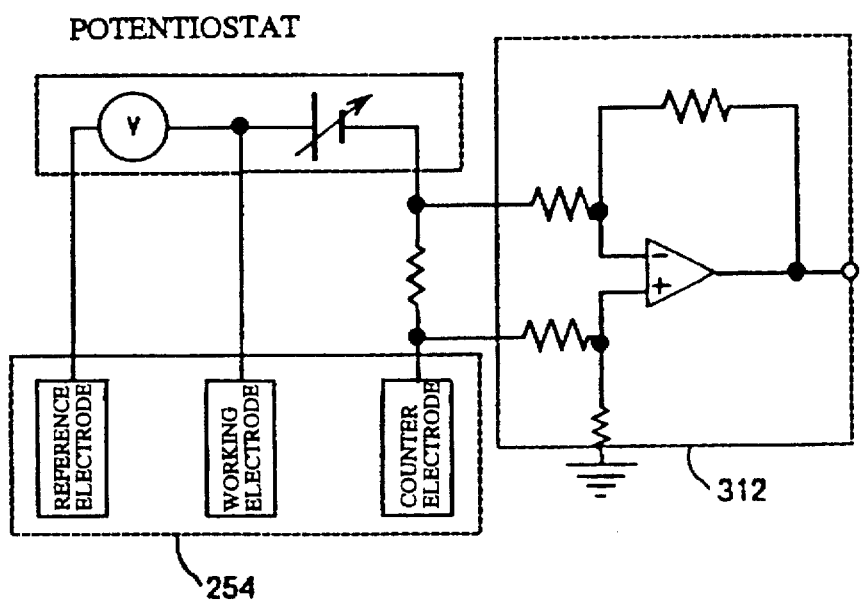
FIG. 16 is a wiring diagram of the electrodes of the flow cell as connected to a potentiostat and an amplifier.

As shown in FIG. 16, during the quantitative analysis of glucose in urine sample, an electric potential is applied by a potentiostat between the working electrode 268 and the counter electrode 270, the electric potential being controlled by the potentiostat in such a manner that the potential difference of the working electrode 268 with respect to the reference electrode 272 is equal to a predetermined positive value, for example, +0.6 V. The electric current flowing between the working electrode 268 and the counter electrode 270 will vary according to the amount of hydrogen peroxide produced. Therefore, the control circuit 256 detects the amount of generation of hydrogen peroxide by detecting the electric current flowing between the working electrode 268 and the counter electrode 270 and determines the glucose content in the urine sample based on the amount of generation of hydrogen peroxide.

It will be noted that detection of the amount of hydrogen peroxide generated by oxidation of glucose can be carried out with much higher accuracy than detection of the amount of consumption (i.e., decrease) of oxygen that occurs in the reaction represented in formula (1) above. Consequently, according to the invention, a high degree of measurement of glucose content is attainable.

Figure 17:
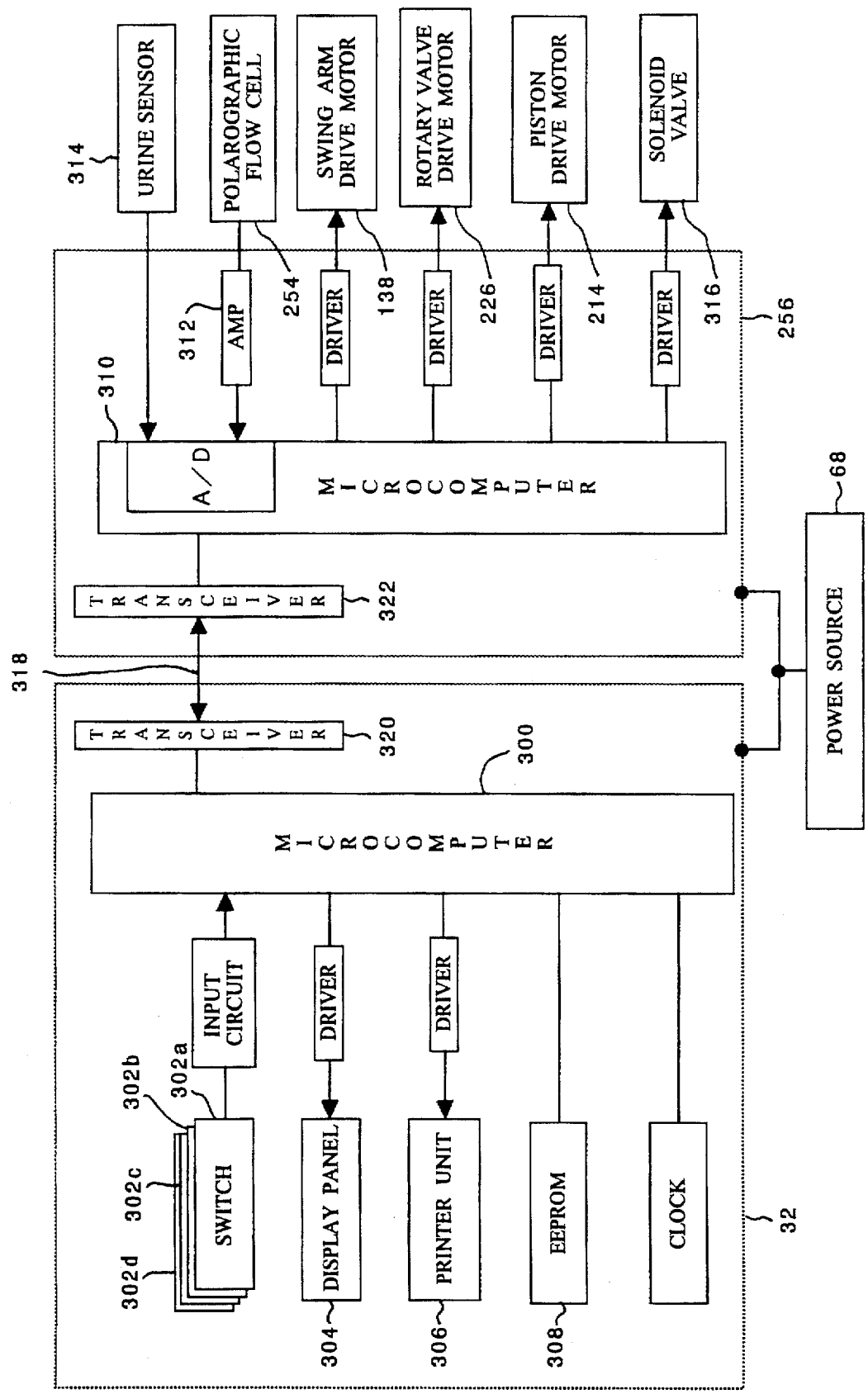
FIG. 17 is a block diagram of a control unit and a control circuit of the urinalysis unit shown in FIG. 1.

In FIG. 17, there are shown examples of the control unit 32 and the control circuit 256. The control unit 32 installed on the side wall of the toilet may comprise a programmed microcomputer 300, a plurality of control switches 302, a liquid crystal display panel 304 for displaying various instructions to the user and the results of urinalysis, a printer unit 306 for outputting the results of urinalysis and the trends of data, and a flash memory device 308 for storing the data of urinalysis. The control switches 302 may separately include a urinalysis start switch 302a for male and a urinalysis start switch 302b for female, the arrangement being such that when the male's switch 302b is depressed the urine sampling vessel 96 is automatically brought to a predetermined male's sampling position (e.g., an appropriate position between the positions B–C of FIG. 8) and that when the female's switch 302b is depressed the urine sampling vessel is brought to a predetermined female's sampling position (e.g., an appropriate position between the positions C–D). The control switches 302 may further include a pair of fine adjustment switches 302c and 302d for finely displacing the urine sampling vessel 96 in the fore-and-aft direction with respect to the predetermined male's or female's position in response to the instructions of the user.

The control circuit 256 includes a microcomputer 310 which is so programmed as to control the components of the urinalysis unit 14 in a manner shown in the flowchart described later. The electric current flowing between the working electrode 268 and the counter electrode 270 of the polarographic cell 254 is amplified by an amplifier 312 and is fed to an analog-to-digital (A/D) converter circuit of the microcomputer 310. A urine sensor 314 is adapted to monitor the electric resistance of the gap defined between the urine detection electrodes 126 and 128 of the urine sampling vessel 96 to see if urine has accumulated in the urine pool 118 of the sampling vessel 96, the output of the urine sensor being delivered to the A/D converter circuit of the microcomputer 310. The microcomputer 310 drives the swing arm drive motor 138, the rotary valve drive motor 226, piston drive motor 214, and a solenoid valve 316 for controlling supply of water to the spray nozzle 162, through respective driver circuits. The microcomputers 300 and 310 are connected with each other by a communication cable 318 to transfer data and signals via transceivers 320 and 322 by serial communication process.

A mode of operation of the urinalysis unit 14 will be described by way of an example with reference also to the schematic view of FIG. 18 and the flowchart of FIGS. 19. As the user presses on the urinalysis start switch 302a or 302b, the microcomputer 310 drives the swing arm drive motor 138 to move the urine sampling vessel 96 to a predetermined urine sampling position and then places the sampling vessel 96 in a desired position in response to the fine adjustment switches 302c or 302d. As positioning of the sampling vessel is thus completed, the user may urinate toward the sampling vessel to have urine sampling started. As accumulation of urine in the urine pool 118 of the sampling vessel 96 is detected based on the signal from the urine sensor 314, the microcomputer 310 energizes the rotary valve drive motor 226 to rotate the rotor 228 until the central port 224 of the syringe pump 52 is brought in registration with the second port 240B of the rotary valve whereby the pumping chamber 212 of the syringe pump 52 is communicated with the urine sampling vessel 96. With the rotary valve in this position, the microcomputer 310 energizes the piston drive motor 214 of the syringe pump 52 to move the piston 210 on the downward stroke to cause about 2 ml, for example, of urine to be drawn into the pumping chamber of the syringe pump 52.

Figure 18:
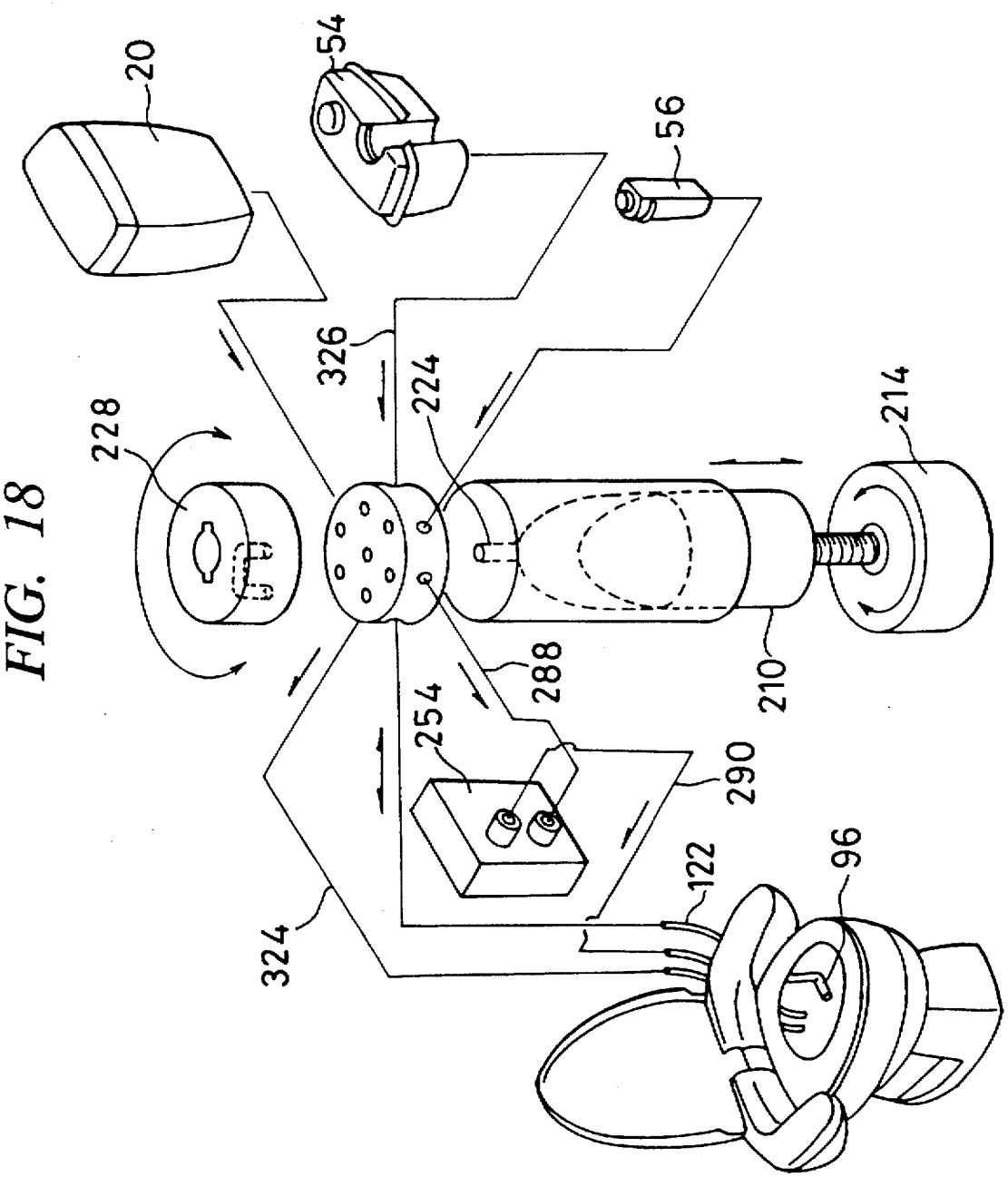
FIG. 18 is a schematic view showing the fluid transfer arrangement of the urinalysis unit shown in FIG. 1.
Figure 19:
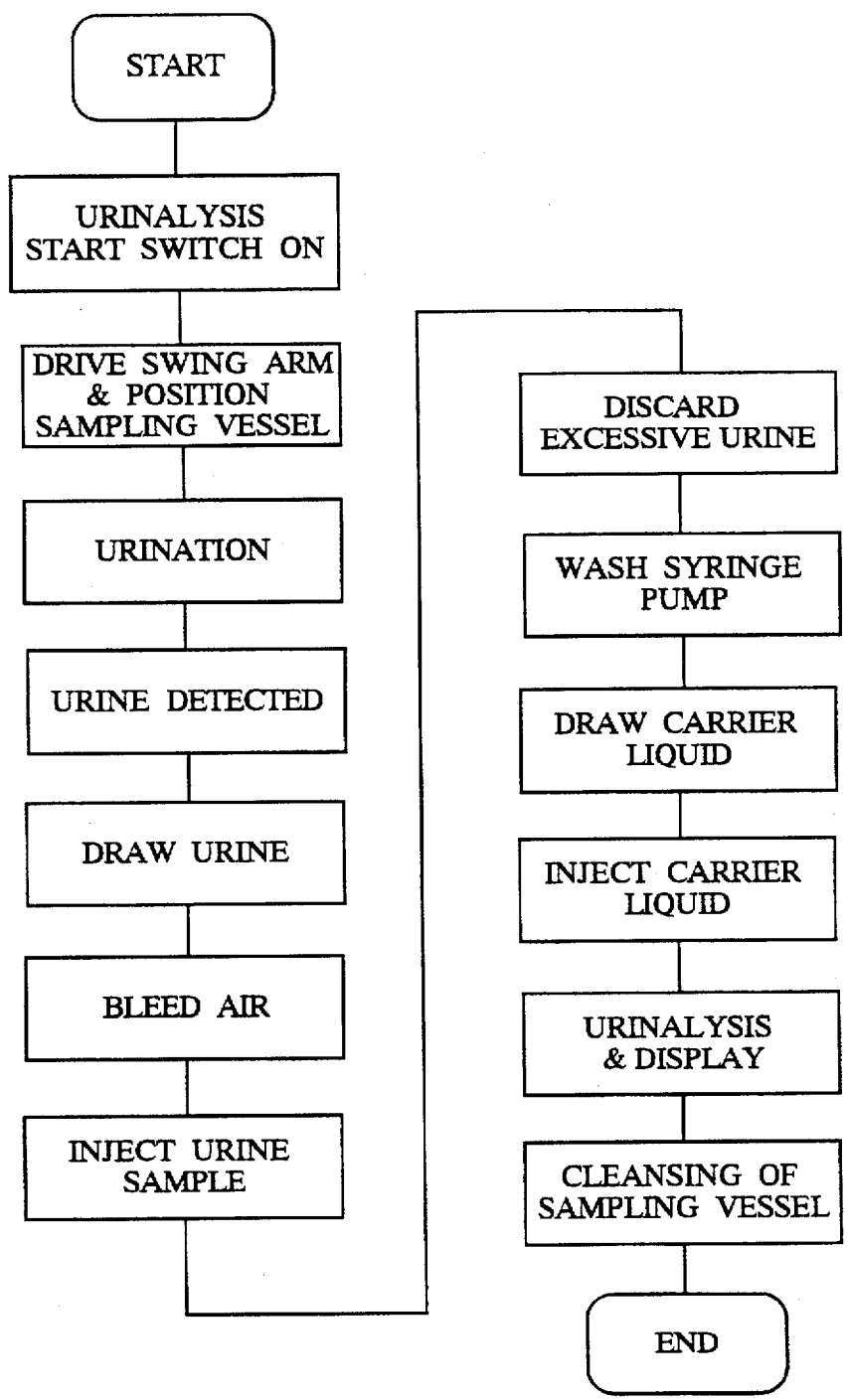
FIG. 19 is a flowchart showing the operation of the urinalysis unit shown in FIG. 1.

Then the rotary valve is again rotated so as to align the central port 224 with the third port 240C of the rotary valve thereby to connect the syringe pump 52 to a discharge conduit 324 shown in FIG. 18. In this state, the piston drive motor 214 is energized to lift the piston of the syringe pump 52 so that a part of urine in the pumping chamber is discharged through the discharge conduit 324 into the bowl of the toilet bowl fixture 12. This permits air bleeding of the pumping chamber so that air bubbles are prevented from being forwarded to the polarographic flow cell 254 even in the event that air has been drawn in the pumping chamber together with urine sample.

The rotary valve is again driven until the central port 224 is aligned with the first port 240A of the rotary valve whereby the pumping chamber 212 is connected to the polarographic flow cell 254. Then the piston of the syringe pump 52 is further lifted until about 10–20 μl of urine sample is injected toward the transfer tube 288. The rotary valve is again rotated to connect the pumping chamber to the discharge conduit 324 whereupon the piston is lifted to the full stroke so as to evacuate the pumping chamber by discarding any excessive urine through the conduit 324 into the bowl 16.

The pumping chamber of the syringe pump 52 is rinsed with water after injection of urine sample. This is done by rotating the rotary valve to connect the pumping chamber of the syringe pump 52 with the cistern 20, by descending the piston to draw water from the cistern into the pumping chamber, by driving the rotary valve to connect the pumping chamber to the discharge conduit 324, and by lifting the piston. Rinsing of the pumping chamber may be carried out for more than a cycle.

Then the rotary valve is again rotated until the central port 224 of the syringe pump 52 is aligned with the fifth port 240E of the rotary valve to communicate the syringe pump 52 through a conduit 326 with the carrier liquid reservoir 54. The carrier liquid in the reservoir 54 serves to transfer the urine sample to the polarographic flow cell 254 as well as to dilute the urine sample delivered to the flow cell 254. The carrier liquid also serves as a buffer solution that provides buffer effect necessary for the stable operation of the polarographic flow cell. To this end, the carrier liquid may contain various additives including hydrogen ion concentration conditioning agent such as $KH_2PO_4$ and $Na_2HPO_4$, chlorine ion intensity conditioning agent such as KCl, and antiseptic. When the syringe pump 52 is connected to the carrier liquid reservoir 54 as mentioned before, the syringe pump 52 is operated to draw the carrier liquid from the reservoir 54 into the pumping chamber 212. The rotary valve is again rotated and the piston 210 is lifted to inject the carrier liquid toward the first port 240A whereby 10–20 µl of urine sample previously injected into the transfer tube 288 is transferred to the polarographic flow cell 254 while being mixed with and diluted by the carrier liquid, the mixture traversed the flow cell being discharged through the transfer tube 290 into the bowl of the toilet. The speed of injection of the carrier liquid may be controlled such that the urine sample flows past the flow cell after it is diluted by the carrier liquid for at least 30 folds. The amount of injection of the carrier liquid may be selected to be about 2–4 ml per cycle. With this amount, the transfer tube 288 as well as the polarographic flow cell 254 will be filled again with fresh carrier liquid after the mixture of urine sample and carrier liquid has flown past the flow cell.

As the mixture of urine sample and carrier liquid flows past the polarographic flow cell 254, hydrogen peroxide will be generated at the GOD fixed membrane 298 of the working electrode 268 as expressed in formula (1) above in an amount proportional to the glucose content in the mixture so that an electric current indicative of the amount of generation of hydrogen peroxide will flow between the working electrode 268 and the counter electrode 270 as described before. The electric current is amplified by the amplifier 312 and is sent to the A/D converter circuit of the microcomputer 310 for conversion into a digital datum which is transmitted to the microcomputer 300 of the control unit 32 by serial communication. The microcomputer 300 computes the urinal glucose content based on the digital datum representing the electric current and displays it on the display panel 304. The data of urinal glucose content are also stored in the flash memory 308. The microcomputer 300 is also programmed to derive the trend of urinalysis and to output it through the printer unit 306 in response to the instructions of the user.

Upon completion of urinalysis or urine sampling, the microcomputer 310 energizes the swing arm drive motor 138 to return the sampling vessel 96 to the storage position A shown in FIG. 8. Then the solenoid valve 316 is open to supply water under pressure to the spray nozzle 162 whereby the sampling vessel 96 is cleansed with water.

As the polarographic flow cell 254 is designed to issue an extremely weak electric current flowing between the working electrode 268 and the counter electrode 270 thereof, it is preferable to electrically insulate the flow cell 254 in order to avoid influence of any undesirable electrical noise. To this end, it is desirable to electrically isolate the transfer tube 290 connected to the flow cell 254 and the discharge conduit 324 connected to the syringe pump 52 from one another and to position the ends thereof, which are located within the bowl 16, at a level higher than the water level in the bowl. Furthermore, the ends of the transfer tube 290 and the discharge conduit 324 located within the bowl are preferably positioned at an equal level so as to avoid any undesirable effect due to gravity.

As urinalysis is repeated, the activity of glucose oxidase in the enzyme fixed membrane 298 of the polarographic flow cell 254 will be degraded so that the output of the flow cell will be decreased as time elapses. Therefore, it is desirable to periodically calibrate the flow cell output. To this end, a calibration solution consisting of a standard glucose solution of a given known glucose concentration is stored in the reservoir 56 and is periodically forwarded to the flow cell in place of the urine sample to periodically detect and measure the flow cell output with respect to the standard glucose solution. During actual urinalysis, the flow cell output for the urine sample may be compensated for in accordance with the flow cell output with respect to the standard glucose solution to derive the urinal glucose content. At the end of a predetermined service life of the flow cell 254, the used flow cell 254 may be detached from the socket 252 and readily replaced with a new one. Electrical as well as hydraulic connection between the flow cell and the socket are carried out in an easy manner by simply urging the flow cell against the socket since the nipples 282, the associated connection bores 286, the pins 276 and the associated pin receptacle holes 292 are arranged to extend perpendicular to the mating faces of the flow cell 254 and the socket 252.

Figure 20:
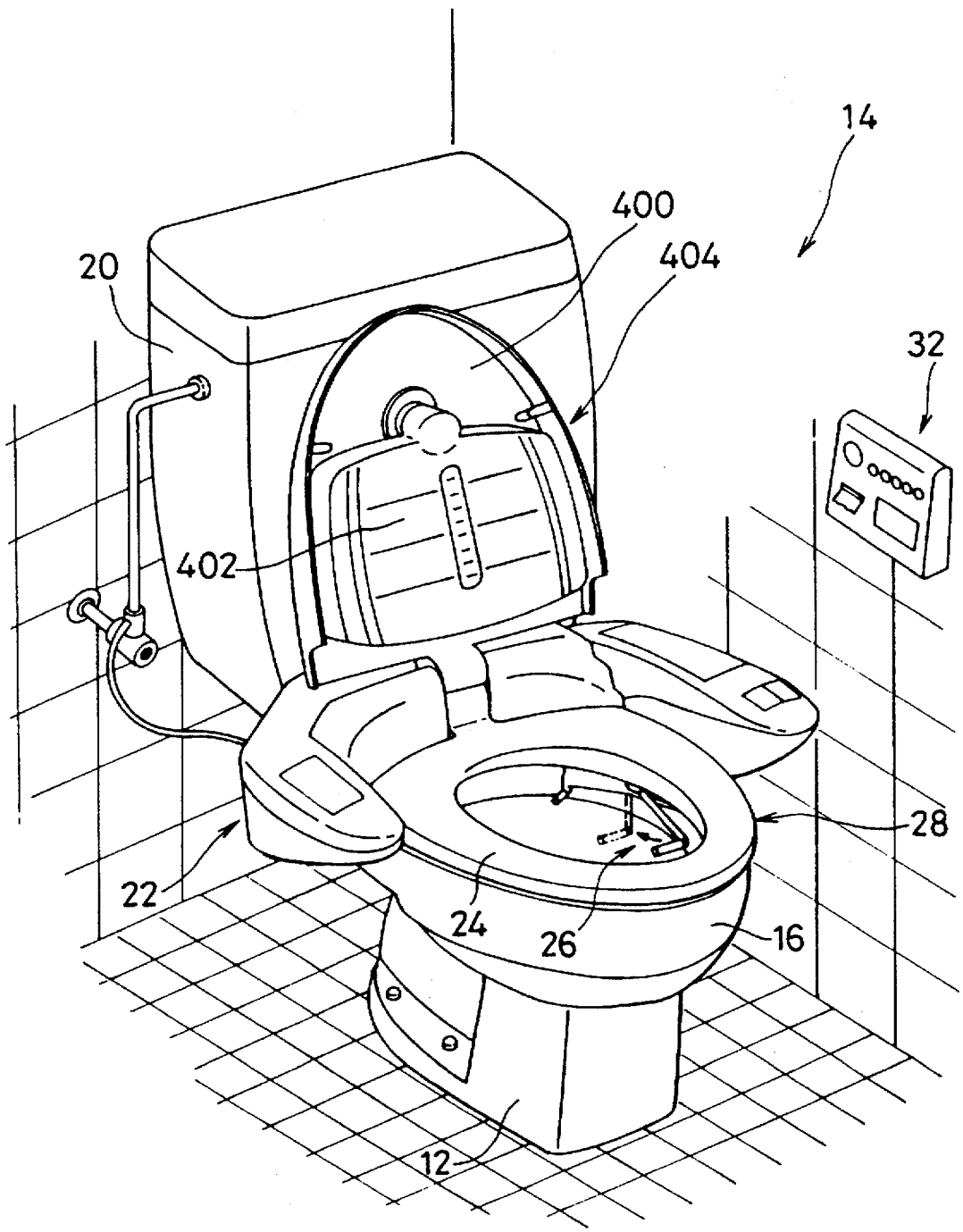
FIG. 20 is a view similar to FIG. 1 but illustrating another layout of the carrier liquid reservoir.
Figure 21:
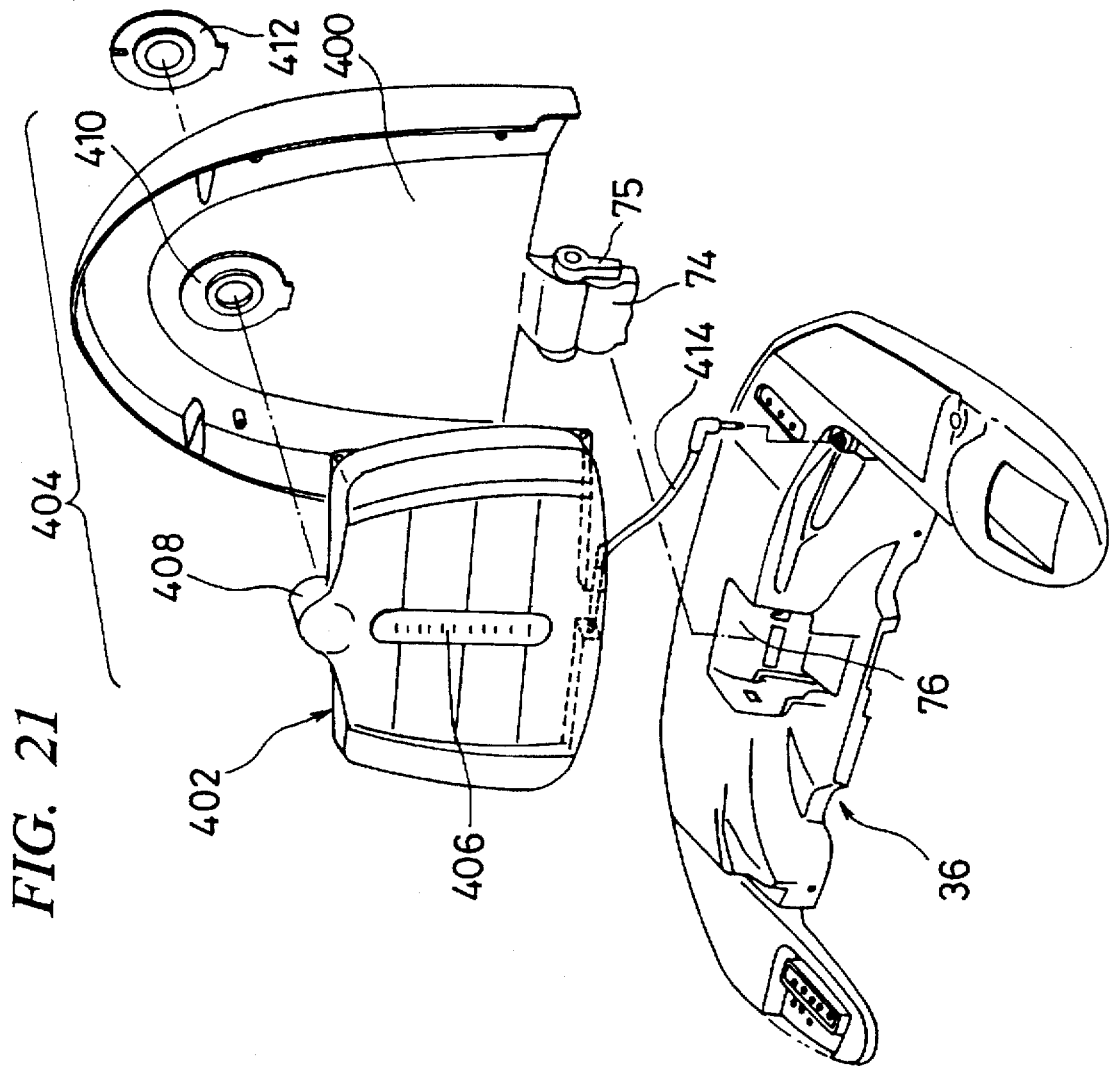
FIG. 21 is an exploded view of the combined toilet lid and carrier liquid reservoir shown in FIG. 20.

FIGS. 20 and 21 illustrate another layout of the urinalysis unit. The feature of this layout is that the carrier liquid reservoir is incorporated in the toilet lid. The toilet lid is hinged to the housing 22 by a retainer block 75 in a manner similar to the first embodiment. Parts and members identical or similar to the foregoing embodiment are indicated by like reference numerals and only the differences will be described. As shown in FIGS. 20 and 21, a carrier liquid reservoir 402 is mounted to a toilet lid 400 by screws and the like to form a combined lid and reservoir assembly 404. The carrier liquid reservoir 402 has a generally flat configuration suitable to be accommodated inside of the toilet lid 400 and is made, for example, by blow molding of plastics. To facilitate inspection of the amount of carrier liquid remaining in the reservoir, the reservoir 402 is made from a generally transparent material. Alternatively, at least a part of the reservoir, such as the portion forming a scale 406, may be made transparent or opaque.

The reservoir 402 is provided at the upper part thereof with an inlet 408 which extends through a fitting 410 attached to the toilet lid 400 and is open onto the upper surface of the toilet lid, the inlet being closed by a detachable filler cap 412. When the toilet lid is swung up as shown in FIG. 20, the carrier liquid reservoir 402 is held in a vertical position so that the residual amount of the carrier liquid is readily observed. When the toilet lid is rotated in a horizontal position, the filler cap 412 may be removed to replenish the carrier liquid. The carrier liquid in the reservoir 402 is fed through a hose 414 to the syringe pump 52 described before.

As in this manner the carrier liquid reservoir 402 is mounted to the toilet lid, a large storage capacity is secured.

Accordingly, the frequency of replenishment of the carrier liquid is minimized so that the maintenance is further simplified. As it will suffice to install only the urinalysis device and the syringe pump in the housing 22, the housing 22 may be made small and compact. Since the carrier liquid reservoir 402 is rotated conjointly with the toilet lid, the reservoir will resume a generally vertical position when the toilet lid is swung up. This facilitates inspection of the residual amount of carrier liquid.

Figure 22:
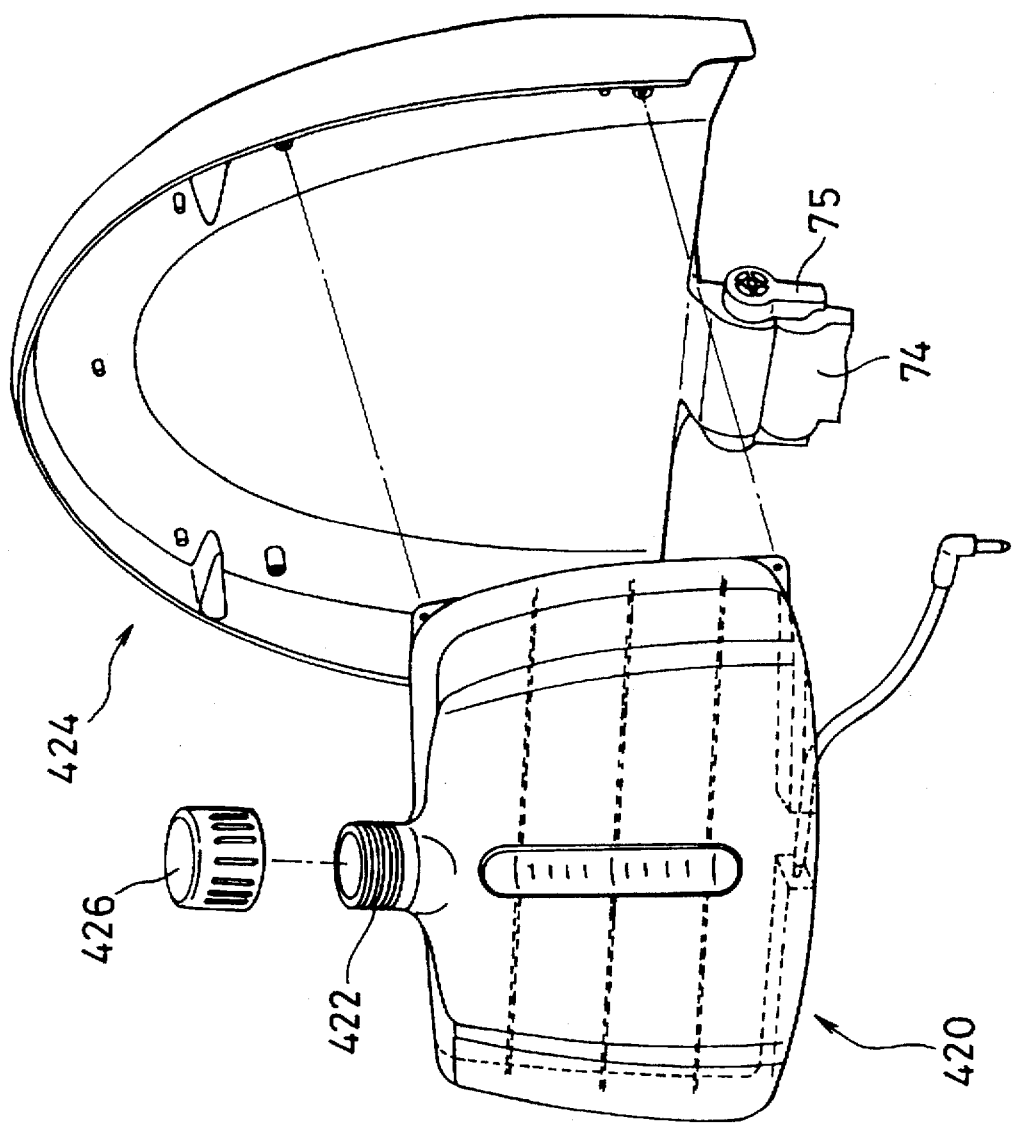
FIG. 22 is an exploded view showing another embodiment of the combined toilet lid and carrier liquid reservoir.

FIG. 22 illustrates a modified embodiment of the combined toilet lid and reservoir assembly. In this embodiment, the carrier liquid inlet 422 of the carrier liquid reservoir 420 is disposed inside of the toilet lid 424 to ensure that the filler cap 426 is removed for replenishment of the carrier liquid when the combined toilet lid and reservoir assembly is swung up in the upright position. This embodiment is advantageous in preventing overflow of carrier liquid as replenishment may be carried out while observing the liquid level in the reservoir with the toilet lid in its vertically swung-up position.

Figure 23:
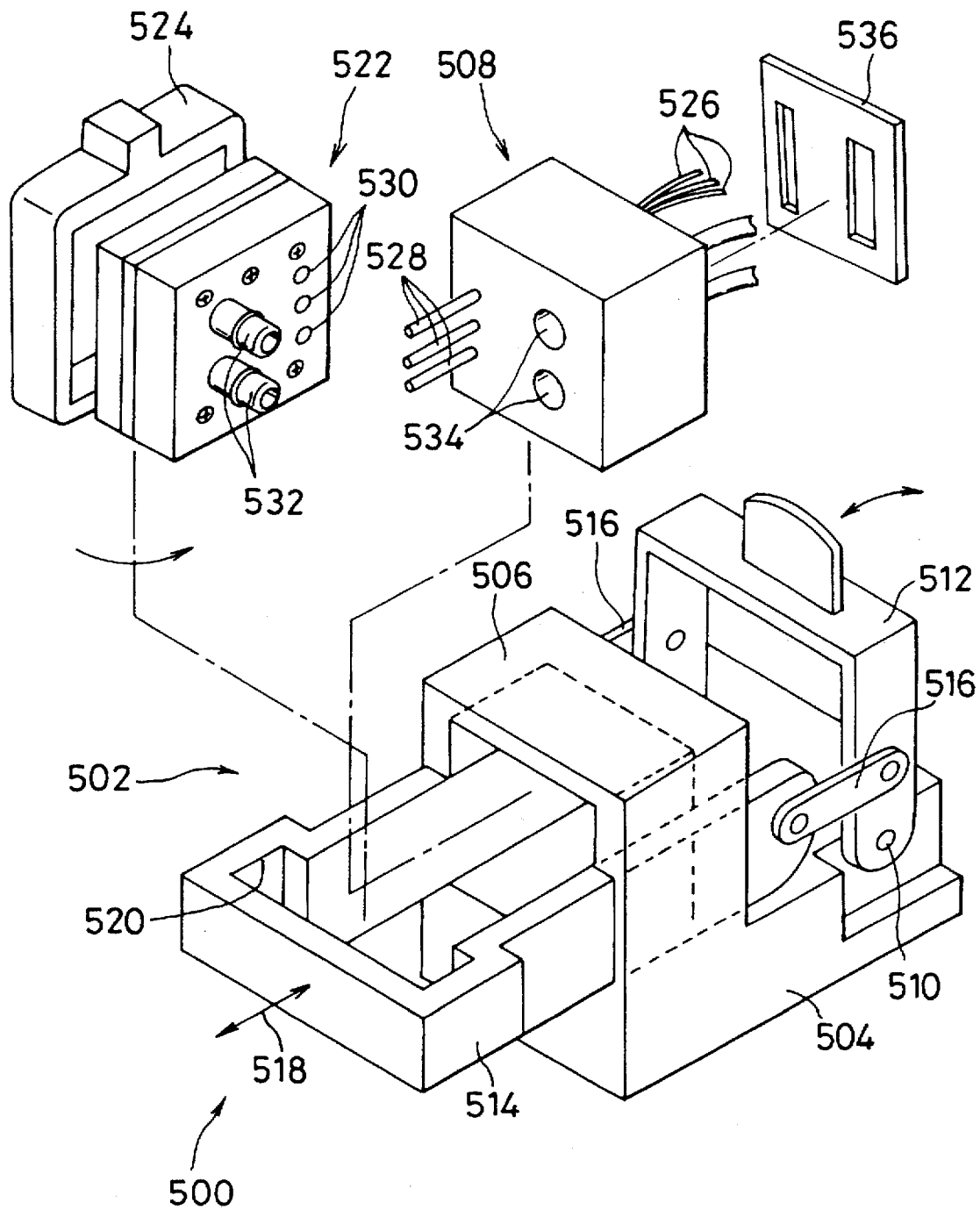
FIG. 23 is an exploded view showing another embodiment of the urinalysis device.

FIG. 23 shows another embodiment of the urinalysis device described before with reference to FIGS. 12–16. This embodiment is designed to facilitate replacement of the disposable polarographic flow cell. Referring to FIG. 23, the urinalysis device 500 includes a clamp mechanism 502 having a base 504 suitably fixed to the frame 34 of the housing 22 in a manner similar to the foregoing embodiment. The base 504 is formed with a socket holder 506 in which a socket block 508 is fitted and is secured by screws, not shown. An operating lever 512 is pivotally mounted to the base 504 by a pair of pivots 510. A slider 514 is slidably mounted to the base 504 and is guided by the socket holder 506. The slider 514 is coupled to the lever 512 by a pair of pivoted links 516 in such a manner that the slider 514 is displaced as shown by the arrow 518 in response the swinging movement of the lever 512. The slider 514 is provided with a notch 520 in which a flow cell holder 524 loaded with a flow cell 522 is detachably fitted.

The flow cell 522 and the socket block 508 therefor are basically similar to those described with reference to FIGS. 12–16 and, therefore, need not be described again in detail. To describe only the differences, in this embodiment, the connecting pins 528 for connecting the electrodes of the flow cell 522 to the lead wires 526 of the socket 508 are fixed to the socket 508 and the associated pin receptacle holes 530 are provided in the flow cell 522. Each pin 528 is adapted to be brought in contact with the associated terminal of the electrode of the flow cell when the latter is mounted to the socket block 508. As in this way the pins are arranged on the socket 508, the disposable flow cell may be manufactured at lower costs. The nipples 532 and the associated connection bores 534 for connecting the electrolytic chamber of the flow cell 522 to the tubes 288 and 290 extending, respectively, to the syringe pump and the bowl are arranged, respectively, on the flow cell and the socket similarly to the foregoing embodiment. A circuit board 536 supporting the control circuit 256 mentioned before is fixed at the back of the socket block 508.

To replace the flow cell 522, a swingable cover 538 provided on the upper casing 36 of the housing 22 as shown in FIG. 2 is opened and the operating lever 512 is rotated in the counter-clockwise direction as viewed in FIG. 23 to disconnect the flow cell 522 from the socket 508. Then the holder 524 as loaded with the flow cell is dismounted from the slider 514 and the used flow cell is removed from the holder and is discarded. Then a new flow cell is loaded on the holder 524 which is then fitted within the notch 520 of the slider 514. Upon turning the lever 512 in the clockwise direction, the new flow cell 522 will be fitted to the socket block 508.

As the nipples 532, the associated connection bores 534, the pins 528 and the associated pin receptacle holes 530 are all arranged to extend perpendicular to the mating faces of the flow cell 522 and the socket 508 in the direction of mounting and dismounting of the flow cell 252 shown by the arrow 518, electrical and hydraulic connection between the flow cell 522 and the socket 508 are completed only by actuating the lever 512. Accordingly, replacement of the flow cell can readily be carried out by an ordinary user. Furthermore, due to the provision of the clamp mechanism 502, it is easy for anyone to securely mount the flow cell even in a narrow toilet room so that any malfunction due to failure of good electrical or hydraulic connection is avoided.

The electrolytic chamber of the unused flow cell may be filled in advance with a carrier liquid containing pH conditioning agent, chlorine ion intensity conditioning agent and antiseptic, with the nipples 538 and the receptacle holes 538 of the flow cell 522 being sealed by rubber caps or plugs. This advantageously sustains the activity of the enzyme and facilitates handling of the flow cell during transportation and storage.

FIGS. 24–29 illustrate another embodiment of the urine sampling device. The feature of this embodiment is that the drive mechanism for the swing arm is simplified to the extent that the urine sampling vessel is displaced only by the rotational movement of the swing arm. In addition, the urine sampling vessel when not in use is adapted to be stored in the vicinity of the inner periphery of the frontal part of the rim of the toilet bowl fixture.

Figure 24:
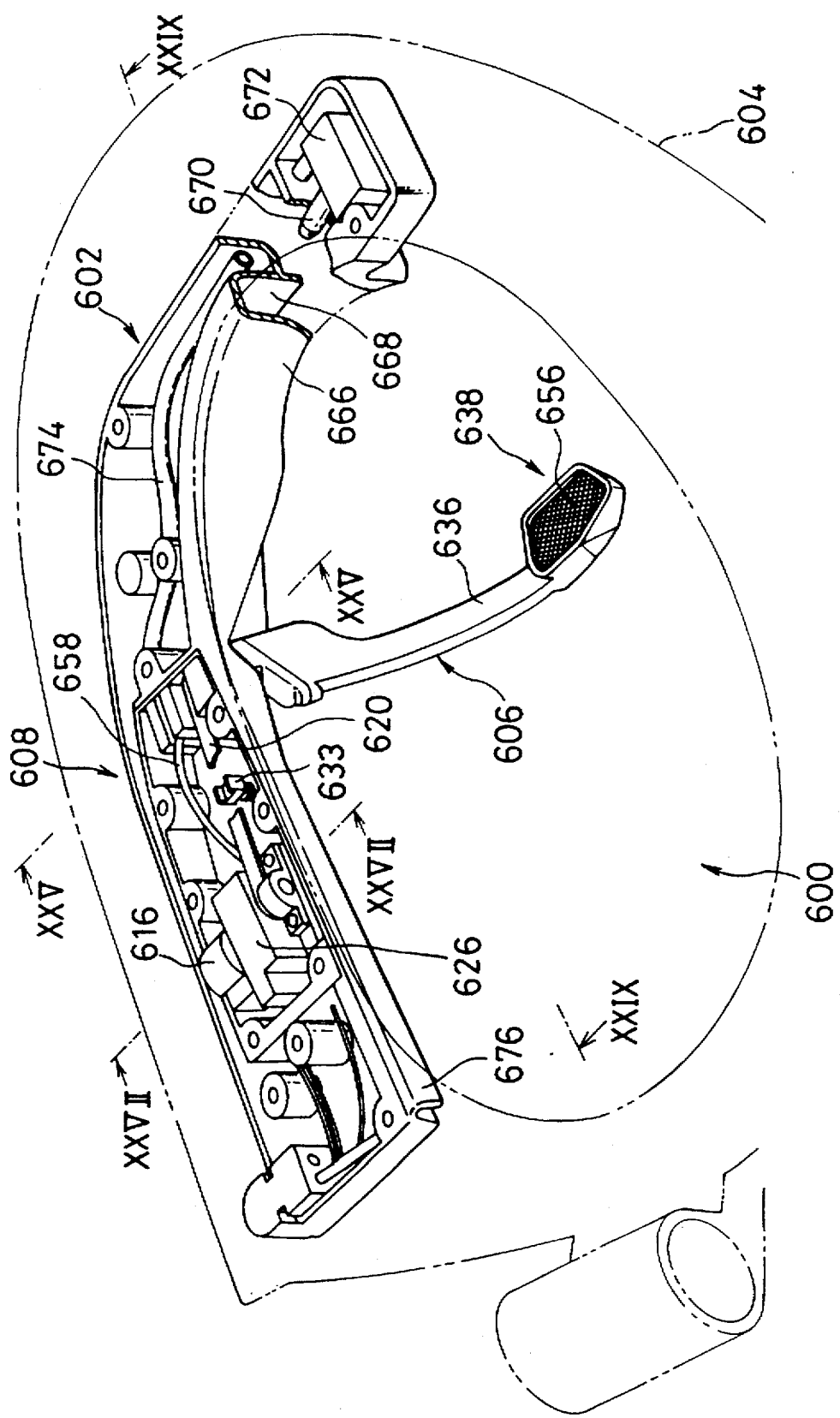
FIG. 24 is a perspective view, partly cut away, showing another embodiment of the urine sampling device, with the toilet seat being shown by phantom line.
Figure 25:
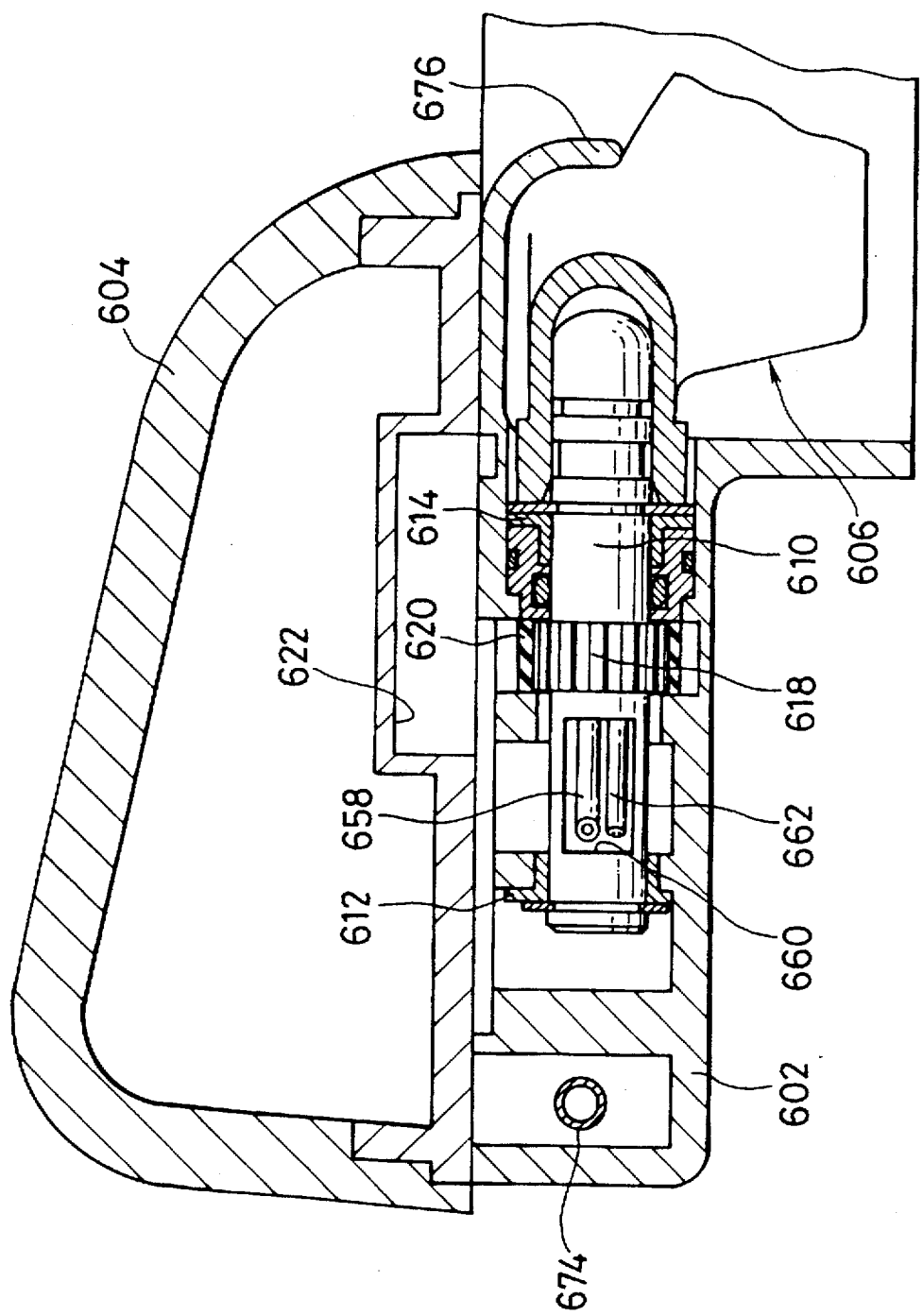
FIG. 25 is a cross-sectional view taken along the line XXV—XXV of FIG. 24.

Referring to FIG. 24, the urine sampling device 600 includes a frame 602 which is suitably secured to the underside of the toilet seat 604 by means such as screws. The frame 602 is arcuated along the contour of the toilet seat in such a manner as to be substantially concealed beneath the toilet seat when affixed to the seat. A swing arm 606 is swingably mounted to the frame 602 and is adapted to be moved by a swing arm drive 608. To this end, the swing arm 606 is provided with a spindle 610 which is rotatably supported by the frame 602 by a pair of bearings 612 and 614 as best shown in FIG. 25. The spindle 610 is rotated by a stepping motor 616 via a belt drive. To this end, the spindle 610 is provided with a driven gear 618 which is held in engagement with a cogged belt 620.

Figure 26:
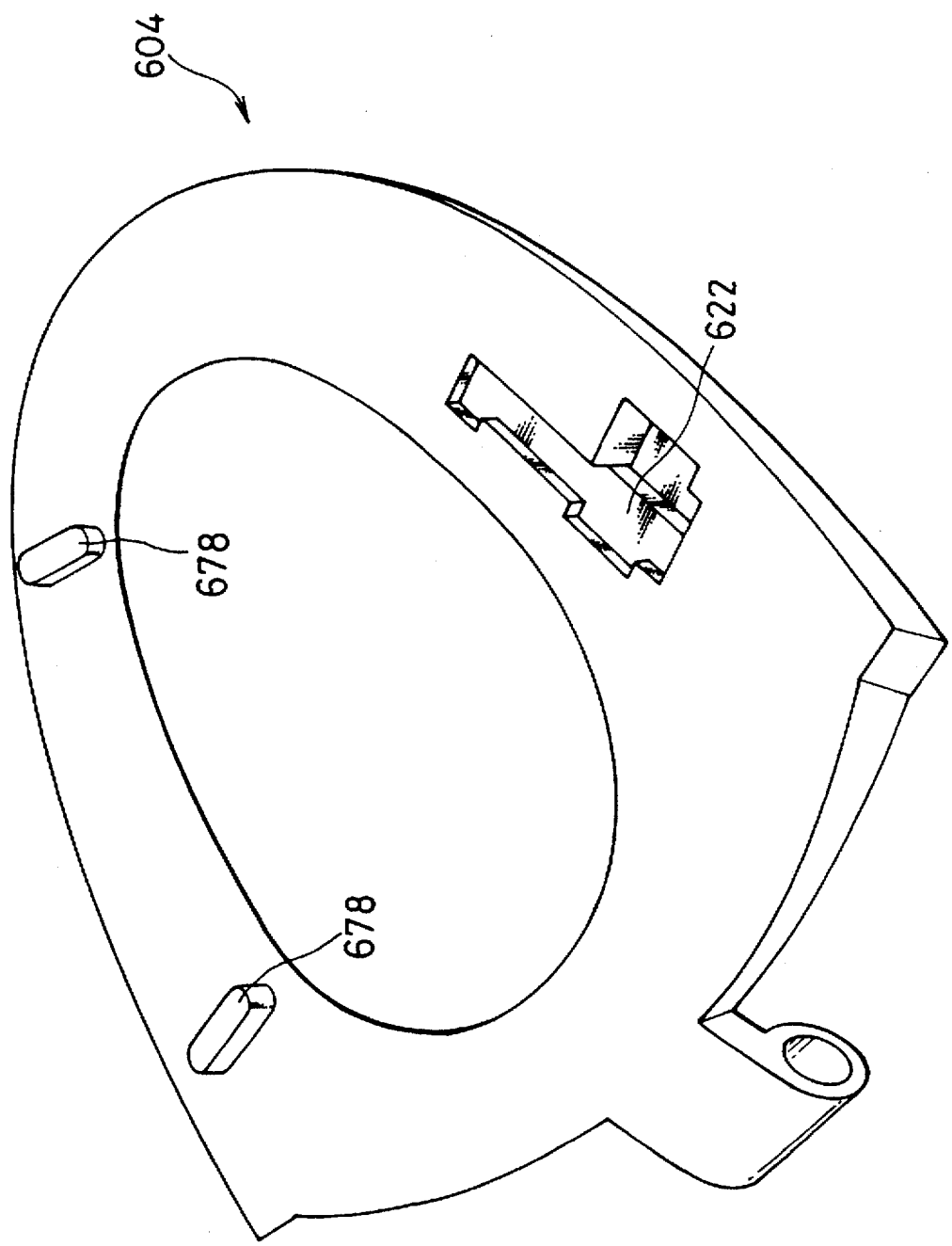
FIG. 26 is a perspective view of the toilet seat of FIG. 24 as reversed.

As will be apparent from FIG. 24, the motor 616 is arranged rearwardly of, and is spaced considerably away from, the spindle 610 of the swing arm 606. As shown in FIG. 26, the toilet seat 604 is provided at the underside thereof with a concavity 622 which is adapted to accommodate the upper parts of the motor 616 and the belt 620. Since the motor 616 is arranged in this manner rearwardly of the frame and the concavity 622 is correspondingly formed in the rear part of the toilet seat 604 in which an increased thickness of the seat is available, it is possible to enlarge the size of the concavity 622 and, hence, to install a larger motor.

Figure 27:
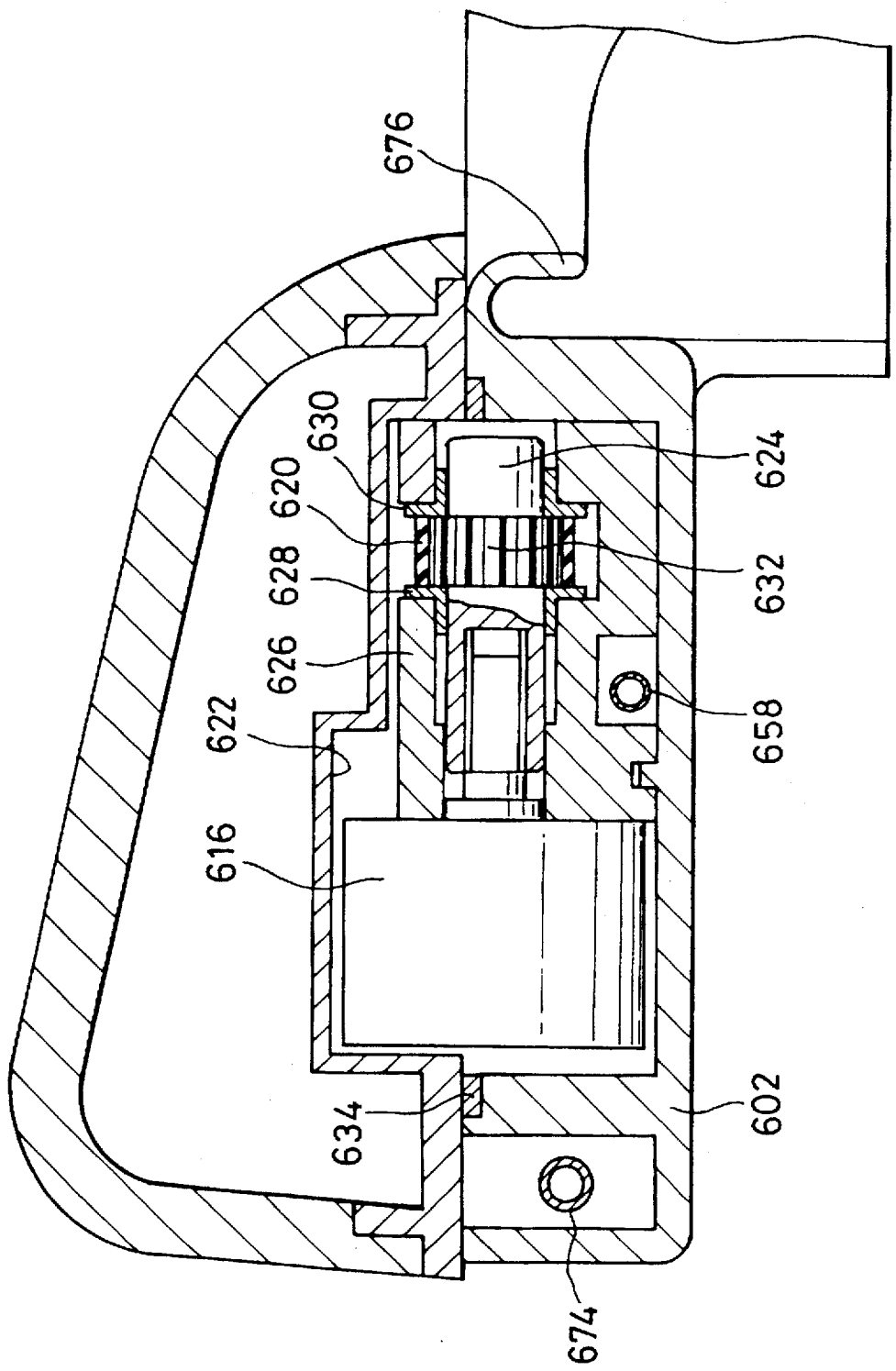
FIG. 27 is a cross-sectional view taken along the line XXVII—XXVII of FIG. 24.

As shown in FIG. 27, an output shaft of the motor 616 is splined to a spindle 624 which is rotatably supported through a pair of bearings 628 and 630 by a bearing block 626 secured to the frame 602. The spindle 626 is provided with a driving gear 632 engaged by the belt 620. As a result, the swing arm 606 will be rotated in response to the rotation of the motor 616. In order to precisely control the angular position of the swing arm, it is desirable to take up any slack in the belt 620. For this reason, an upwardly spring biased slider 633 is arranged on the frame 602 and a conventional tension pulley, not shown for simplicity of drawing, is mounted on the slider in such a manner as to engage the lower run of the belt 620, as shown in FIG. 24. The space which houses the motor 616 and the belt drive is sealed in a waterproof fashion by a packing 634 sandwiched between the frame 602 and the lower surface of the toilet seat.

The swing arm 606 is provided at its lower end 636 with a urine sampling vessel 638. As will be apparent from FIG. 24, the lower end 636 of the swing arm 606 is rearwardly offset in a staggered fashion with respect to the spindle 610 to ensure that the urine sampling vessel 638 is positioned rearwardly as far as possible when the swing arm 606 is rotated to the rearmost extremity position.

Figure 28:
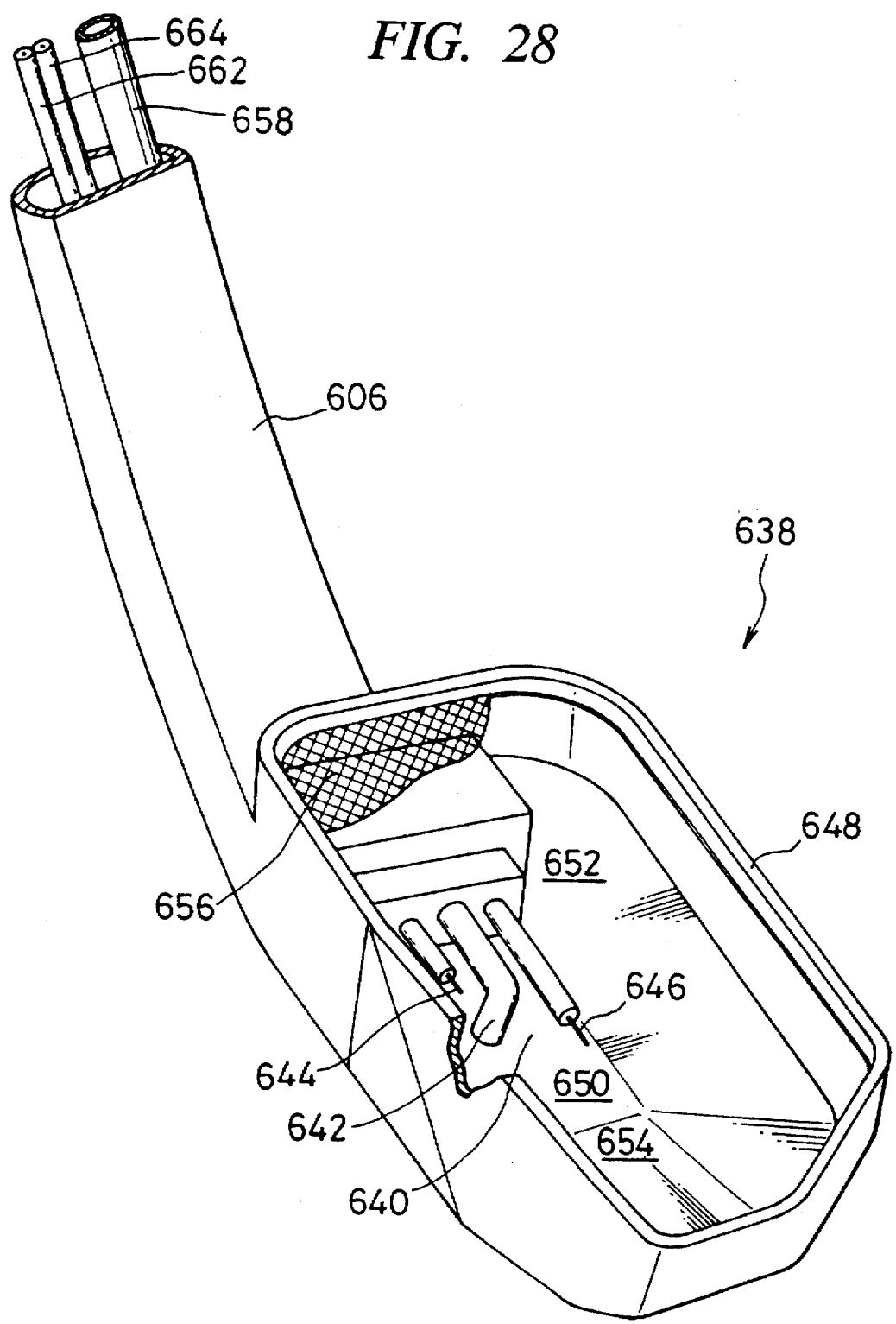
FIG. 28 is an enlarged perspective view, partly cut away, of the sampling vessel shown in FIG. 24; and, FIG. 29 is a cross-sectional view taken along the line XXIX—XXIX of FIG. 24 and showing the swing arm and the urine sampling vessel in various different positions.

As best shown in FIG. 28, the urine sampling vessel 638 has a shallow bilge-like configuration extending transversely of the toilet bowl fixture and is provided at the bottom thereof with a urine pool 640. Similar to the embodiment shown in FIG. 7, an L-shaped suction pipe 642 opens toward the bottom of the urine pool 640 and a pair of sheathed electrodes 644 and 646 project into the urine pool. In the illustrated embodiment, the urine sampling vessel 638 is comprised of an upright annular side wall 648, a bottom wall 650, a front wall 652 inclined rearwardly toward the bottom wall 650, and a right-hand wall 654 inclined leftwards toward the bottom wall 650, the urine sampling vessel 638 as a whole presenting a generally flat configuration.

The inlet opening of the urine sampling vessel 638 is covered by a metallic screen 656 similarly to the embodiment shown in FIG. 7 to prevent splash of urine impinging upon the urine sampling vessel 638. The L-shaped suction pipe 642 is connected to a flexible tube 658 extending through the inner space of the hollow swing arm 606. The tube 658 is further extended through the inner space of the hollow spindle 610 and is directed rearwardly through a window 660 in the spindle 610 as shown in FIG. 25 for connection to the syringe pump. Similarly, the urine sensing electrodes 644 and 646 are connected, respectively, to lead wires 662 and 664 that extend the inner spaces of the swing arm and the spindle 610. These lead wires are connected to the control circuit of the urinalysis device in a manner described before.

As shown in FIG. 24, the frame 602 of the urine sampling device 600 extends along the contour of the toilet seat up to the frontal part of the toilet seat. As will be apparent from FIGS. 24 and 29, the frame 602 is formed with a channel-shaped wall 666 defining a storage and washing chamber 668 open downwardly toward the toilet bowl. A spray nozzle 670 is directed toward the storage and washing chamber 668 to inject water under pressure toward the urine sampling vessel 638 as returned to the position indicated by the solid line in FIG. 29 so as to cleanse the urine sampling vessel 638 after use. The spray nozzle 670 may be secured to a mounting block 672 fixed to the frame 602 and may be supplied with water under pressure through a water hose 674 connected via a solenoid valve to a water line in a manner similar to the foregoing embodiment. The size of the channel-shaped wall 666 is decreased at the rear part to form a drainage trough 676.

Figure 29:
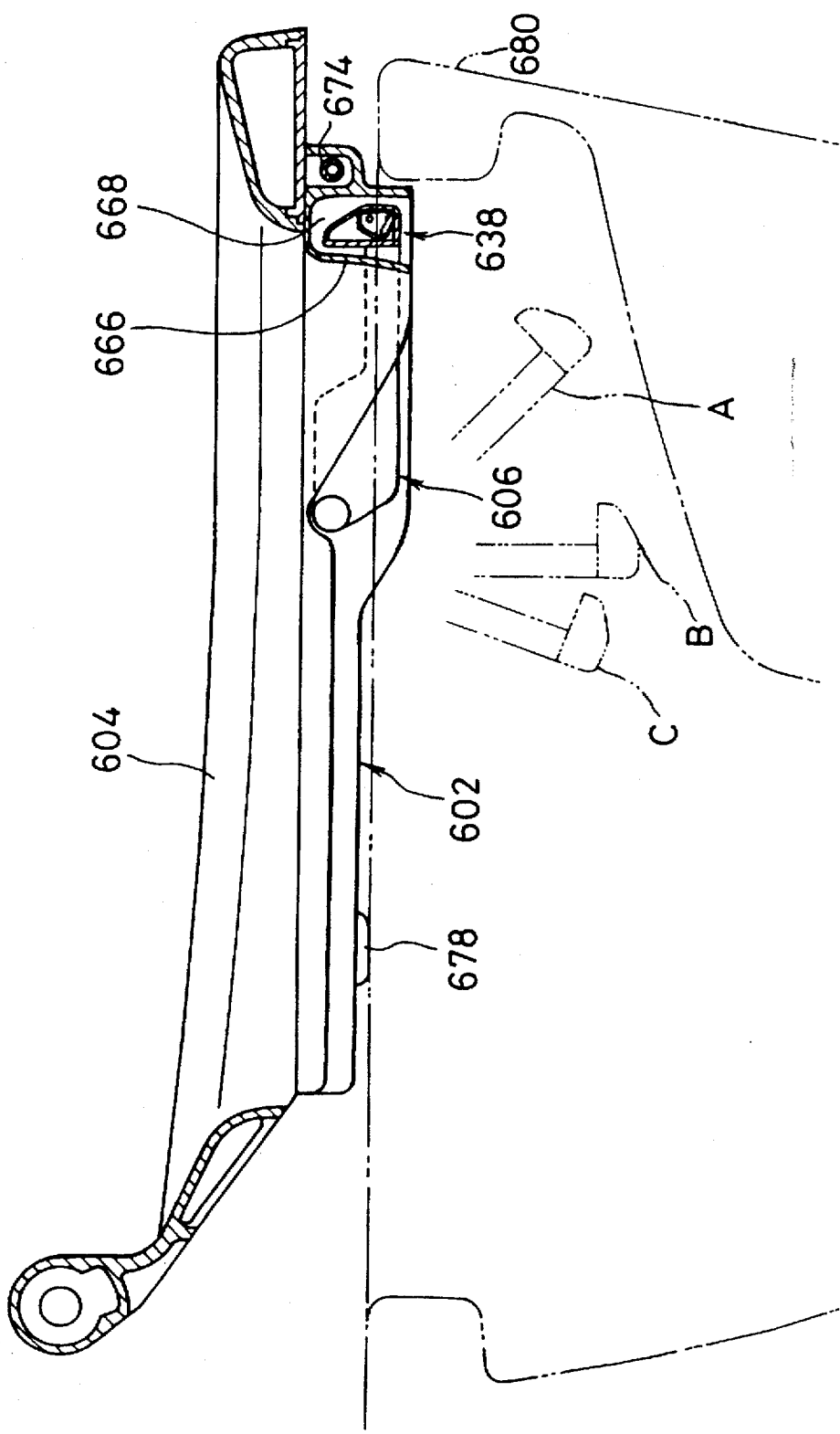

When not in use, the urine sampling vessel 638 is positioned within the storage and washing chamber 668 as shown by the solid line in FIG. 29 so that the toilet seat 604 can be rotated together with the urine sampling vessel 638. Similar to the foregoing embodiment, the toilet seat 604 in its operative position rests upon the rim 680 of the bowl fixture by way of cushioned support legs, two of which are indicated in FIG. 26 by the reference numeral 678, with the other two, not shown, being arranged at the underside of the frame 602.

Since the urine sampling vessel 638 is made substantially flat, it will assume a generally vertical position when stored in the storage and washing chamber 668 as shown by the solid line in FIG. 29, so that the urine sampling vessel 638 can readily be stored in the narrow washing chamber 668. As a result, it is possible to minimize the fore-and-aft dimension of the storage and washing chamber 668 to ensure that the washing chamber 668 is concealed under the toilet seat 604 as far as possible to provide a toilet seat assembly which has a neat appearance.

For sampling of urine released from a male user, the urine sampling vessel 638 may be positioned in the vicinity of the position A shown by the imaginary line in FIG. 29. In this position, the inlet opening of the urine sampling vessel 638 is inclined forwardly so that the urine column ejected forwardly from the user's penis and tending to fall upon the relatively frontal part of the toilet bowl will intersect the inlet opening of the urine sampling vessel 638 generally perpendicularly thereto. Accordingly, the urine sampling vessel 638 receives urine by utilizing the full area of the inlet opening.

In the case of female, urine column tends to fall rearwardly of the bowl as opposed to male's position. Therefore, when the user is female, the urine sampling vessel 638 may be positioned in the vicinity of the position B shown by the imaginary line. In this position, the inlet opening of the urine sampling vessel 638 will assume a generally horizontal posture. The inclined frontal and right-hand walls 652 and 654 will effectively receive urine impinging on the urine sampling vessel 638 and will serve to direct it to flow toward the urine pool 640. The urine sampling vessel 638 may occasionally be moved to the extremity position C according to the instructions of the user.

After urine sampling, the urine sampling vessel 638 is returned to the position shown by the solid line in FIG. 29. Similar to the first embodiment, the solenoid valve is then opened whereby water is ejected from the spray nozzle 670 to wash the urine sampling vessel. Used water is allowed to fall from the downwardly opened storage and washing chamber 668 into the bowl. When the toilet seat is swung up, the residual droplets of cleansing water will be guided by the drainage trough 676 to flow to the rear of the frame and drained into rear part of the bowl 16.

While the present invention has been described herein with reference to the specific embodiments thereof, it is contemplated that the present invention is not limited thereby and various changes and modification may be made therein. For instance, while the polarographic flow cell has been described as being provided with a working electrode having a GOD fixed membrane adapted to analyze urinal glucose, it is also possible to use a flow cell capable of analyzing urinal constituents other than glucose. In addition to or in place of the polarographic flow cell, other type of urinalysis device adapted to perform urinalysis by liquid chromatographic process or colorimetric analysis process may be used, with one or more of the additional urinalysis device being arranged in parallel to the polarographic flow cell. Furthermore, rotary pump or other type of urine transfer system may be adopted instead of the syringe pump. While the control system of the urinalysis unit has been described as comprising the control unit 32 installed on the toilet wall and the control circuit 256 arranged in the housing 22, these parts may be integrated into a single unit.

We claim:

1. A toilet bowl-mounted urinalysis unit for sampling and analysis of urine at a toilet equipped with a standard water closet bowl fixture having a bowl and a flushing water supply section located rearwardly of the bowl, said urinalysis unit comprising:

a housing designed to be mounted in use on the upper surface of said standard bowl fixture between said bowl and said flushing water supply section thereof;

a toilet seat hinged to said housing for swinging movement between a horizontal operative position in which said seat rests upon said bowl fixture and an upright inoperative position;

a urine sampling device, including a movable urine sampling vessel, mounted to said toilet seat for swinging movement conjointly therewith for sampling, in mid-air within the inner space of said bowl, a quantity of urine excreted into said bowl;

a urinalysis device arranged in said housing;

fluid transfer means, including a fluid pump arranged in said housing, for transferring urine sample from said sampling vessel to said urinalysis device;

output means for outputting the results of urinalysis by said urinalysis device; and, control means for controlling said urine sampling device, said fluid transfer means, said urinalysis device and said output means in such a manner that, upon urination into the toilet bowl, urine is sampled and transferred to said urinalysis device and is subjected to urinalysis with the results thereof being output by said output means.

2. A urinalysis unit according to claim 1, wherein said urine sampling device comprises a swingable arm and an electrical drive therefor, said arm having an end supported by said toilet seat for pivoting movement about a horizontal axis and the other end supporting said urine sampling vessel, said electrical drive being operative to move said urine sampling vessel between an operative position situated within the inner space of said bowl and a rest position situated adjacent to the rim of said bowl fixture.

3. A urinalysis unit according to claim 2, wherein said toilet seat is provided at the lower surface thereof with a downwardly directed concavity and wherein said electrical drive is accommodated at least in part in said concavity.

4. A urinalysis unit according to claim 2, wherein said urine sampling device comprises a frame secured to said toilet seat at the lower surface thereof, said frame being confined in a vertical direction within a vertical gap defined between the upper surface of the rim of said bowl and the lower surface of said toilet seat in said horizontal position thereof, said frame being arcuated to extend along said toilet seat in such a manner as to be substantially concealed by said toilet seat.

5. A urinalysis unit according to claim 2, wherein said electrical drive is operative to move said urine sampling vessel along the inner surface of said bowl between an operative position situated adjacent the bottom of said bowl and a rest position situated adjacent to the frontal part of said rim and wherein said urine sampling vessel in its rest position is held adjacent to the frontal part of said rim.

6. A urinalysis unit according to claim 5, wherein said urine sampling vessel in its rest position is substantially concealed underneath said toilet seat when said seat is in its horizontal operative position.

7. A urinalysis unit according to claim 6, wherein said urine sampling device is provided with cleansing means for flushing with water said urine sampling vessel after use.

8. A urinalysis unit according to claim 1, wherein said urinalysis device comprises a polarographic cell responsive to a predetermined constituent of urine to issue an electric signal indicative of the content of said constituent and data processing means responsive to said signal to determine the content of said constituent and wherein said fluid transfer means comprises a reservoir for a carrier fluid and is operable to transfer urine sample as mixed with and diluted by said carrier fluid to said polarographic cell.

9. A urinalysis unit according to claim 8, wherein said carrier fluid reservoir is arranged in said housing.

10. A urinalysis unit according to claim 8, wherein said polarographic cell comprises a working electrode on which an enzyme apt to selectively promote reaction of said predetermined constituent of urine is supported, said polarographic cell being operative to issue an electric signal representing the amount of product of reaction.

11. A urinalysis unit according to claim 10, wherein said enzyme comprises a glucose oxidase and wherein said polarographic cell is operative to issue an electric signal representing the amount of hydrogen peroxide produced by glucose oxidase.

12. A urinalysis unit according to claim 10, wherein said polarographic cell comprises a disposable polarographic flow cell and wherein said urinalysis device comprises a support socket secured to said housing for detachably mounting said flow cell.

13. A urinalysis unit according to claim 12, wherein said support socket comprises a fluid inlet connected to said fluid pump, a fluid outlet and electric lines connected to said data processing means, said socket and flow cell having mating faces extending perpendicular to the direction of mounting of said flow cell against said socket, said socket and flow cell being provided with fluid coupling means for connecting said fluid inlet and outlet to an electrolytic chamber of said flow cell and with electrical connection means for electrically connecting said electric lines to electrodes of said flow cell, said fluid coupling means and said electrical connection means extending perpendicular to said mating faces and parallel to said direction of mounting so that upon movement of said flow cell toward said socket in said direction of mounting, said flow cell and socket are hydraulically and electrically connected with each other.

14. A urinalysis unit according to claim 13, further comprising a clamp mechanism for clamping said flow cell against said socket.

15. A urinalysis unit according to claim 14, wherein said clamp mechanism comprises a flow cell holder for replaceably holding said flow cell and a drive mechanism for displacing said holder in such a manner that said flow cell is moved to and away from said socket.

16. A urinalysis unit according to claim 15, wherein said drive mechanism comprises a levered force amplification mechanism.

17. A urinalysis unit according to claim 13, wherein said mating faces are vertical and wherein said fluid outlet is disposed above said fluid inlet so that air bubbles entered into said electrolytic chamber of said flow cell are readily removed therefrom.

18. A urinalysis unit according to claim 1, further comprising a bidet equipment for producing upwardly-directed spray for washing perineal part of the user, said housing having a central portion extending transversally of said bowl fixture and a lateral portion extending forwardly from an end of said central portion, said urinalysis device and said fluid pump being housed in said lateral portion, said bidet equipment being disposed in said central portion.

19. A urinalysis unit according to claim 1, wherein said urinalysis device comprises a urinalysis flow cell responsive to a predetermined constituent in urine to issue an electric signal indicative of the content of said constituent and data processing means responsive to said signal to determine the content of said constituent; said fluid transfer means comprising a reservoir for a carrier fluid; said fluid pump comprising an electrically driven syringe type pump having a pumping chamber; said fluid transfer means comprising an electrically driven valve having a first port in communication with said pumping chamber, a second port in communication with said urine sampling vessel, a third port in communication with said reservoir for a carrier fluid, and a fourth port in communication with said flow cell; said valve being operative to selectively connect said first port with said second, third or fourth port; said syringe pump and said valve being operative to draw urine sample sampled by said sampling vessel into the pumping chamber of said pump, to inject a metered quantity of urine sample toward said flow cell and to propel the thus injected urine sample by the carrier fluid to flow past said flow cell.

20. A urinalysis unit according to claim 19, wherein said electrically driven valve is a rotary valve.

21. A urinalysis unit according to claim 20, wherein said electrically driven rotary valve and said syringe pump are arranged substantially coaxially with one another to form an integral module.

22. A urinalysis unit according to claim 19, wherein said urinalysis flow cell comprises a polarographic cell having a working electrode on which an enzyme apt to selectively promote reaction of a predetermined constituent in urine sample is supported.

23. A urinalysis unit according to claim 22, wherein said enzyme is operative to oxidize glucose contained in said urine sample and wherein said polarographic cell is operative to issue an electric signal in accordance with the glucose content in urine sample.

24. A urinalysis unit according to claim 19, wherein said electrically driven valve further comprises a fifth port in communication with a source of calibration solution to supply a calibration solution to said urinalysis flow cell.

25. A urinalysis unit according to claim 19, wherein said electrically driven valve further comprises a port in communication with a source of water to supply cleansing water to the pumping chamber of said syringe pump.

26. A urinalysis unit according to claim 1, wherein said urinalysis device comprises a reservoir for a liquid reagent which reacts with a predetermined constituent in urine, a urinalysis flow cell liquid responsive to the reaction of said constituent with said reagent to issue an electric signal indicative of the content of said constituent, and data processing means responsive to said signal to determine the content of said constituent; said fluid pump comprising an electrically driven syringe type pump having a pumping chamber; said fluid transfer means comprising an electrically driven valve having a first port in communication with said pumping chamber, a second port in communication with said urine sampling vessel, a third port in communication with said reservoir for a liquid reagent, and a fourth port in communication with said flow cell; said valve being operative to selectively connect said first port with said second, third or fourth port; said syringe pump and said valve being operative to draw urine sample sampled by said sampling vessel and said liquid reagent into the pumping chamber of said pump and to transfer the mixture of said urine sample and said liquid reagent to said flow cell.

27. A toilet with urinalysis function, comprising:
a standard water closet bowl fixture having a bowl and a flushing water supply section located rearwardly of the bowl;

a housing mounted on the upper surface of said standard bowl fixture between said bowl and said flushing water supply section thereof;

a toilet seat hinged to said housing for swinging movement between a horizontal operative position and an upright inoperative position;

an electrically operated urine sampling device, including a movable urine sampling vessel, mounted to said toilet seat for swinging movement conjointly therewith for sampling, in mid-air within the inner space of said bowl, a quantity of urine excreted into said bowl;

a urinalysis device arranged in said housing;

fluid transfer means, including a fluid pump arranged in said housing, for transferring urine sample from said sampling vessel to said urinalysis device;

output means for outputting the results of urinalysis by said urinalysis device; and, control means for controlling said urine sampling device, said transfer means, said urinalysis device and said output means in such a manner that, upon urination into the toilet bowl, urine is sampled and transferred to said urinalysis device and is subjected to urinalysis with the results thereof being output by said output means.

28. A urinalysis unit for use with a toilet bowl fixture comprising:
a urine sampling device including a collecting portion positionable in an inner space of a toilet bowl fixture for receiving a quantity of urine excreted into the bowl;
a urinalysis device;
fluid transfer means fluidly connecting the urine sampling device and the urinalysis device for transferring urine from the urine sampling device to the urinalysis device;
a support adapted to be mounted on the toilet bowl fixture, the support including an open seating area and means for supporting the urine sampling device, the urinalysis device, and the fluid transfer means.

29. The urinalysis unit of claim 28, wherein the urine sampling device is mounted on the support beneath the seating area.

30. The urinalysis unit of claim 28, wherein the seating area of the support includes a hinged toilet seat movable between a horizontal operative position proximate to the toilet bowl, and an upright inoperative position, and the urine sampling device is mounted on the hinged toilet seat.

31. The urinalysis unit of claim 28, wherein the collecting portion of the urine sampling device is movable into and out of a position for sampling urine in midair within the inner space of the bowl.

32. The urinalysis unit of claim 31, wherein the urine sampling device is mounted on the support beneath the seating area.

33. The urinalysis unit of claim 28, wherein the fluid transfer means includes a fluid pump.

34. The urinalysis unit of claim 28, including output means for outputting urinalysis results from the urinalysis device.

35. The urinalysis unit of claim 28, including control means for controlling the urine sampling device, the fluid transfer means, and the urinalysis device so that upon urination into the toilet bowl, urine is sampled, transferred to the urinalysis device, and subjected to urinalysis.

36. The urinalysis unit of claim 35, including output means for outputting urinalysis results of the urinalysis device.

37. The urinalysis unit of claim 28, wherein the support includes a housing, and the urinalysis device and the fluid transfer means are located in the housing.

38. The urinalysis unit of claim 37, wherein the seating area of the support includes a hinged toilet seat movable between a horizontal operative position proximate to the toilet bowl and an upright inoperative position, and the urine sampling device is mounted on the hinged toilet seat.

39. The urinalysis unit of claim 28, wherein the support is adapted to be mounted on the upper surface of the toilet bowl fixture.

40. The urinalysis unit of claim 39, wherein the support is adapted to be mounted to seat mounting holes in the toilet bowl fixture.

41. The urinalysis unit of claim 28, wherein the support is a single integral self-supporting unit.

42. The urinalysis unit of claim 41, wherein the seating area includes a hinged toilet seat.

43. The urinalysis unit of claim 41, wherein the support includes a housing having portions located alongside the seating area and forming an armrest.

44. The urinalysis unit of claim 43, wherein the housing is C-shaped and surrounds the seating area.

45. The urinalysis unit of claim 28, wherein said support includes a frame for fixed mounting to an underside of a toilet seat, wherein said urine sampling device is mounted to said frame.

46. The urinalysis unit of claim 45, wherein said urine sampling device includes a swing arm swingably mounted at a first end to said frame, and a urine sampling vessel connected to a second end of said swing arm for collecting said urine sample.

47. The urinalysis unit of claim 46, wherein said swing arm rests between said toilet seat and an upper surface of a rim of said toilet bowl.

48. The urinalysis unit of claim 46, further comprising control means for adjusting the position of said swing arm within the inner space according to the gender of a user of said urinalysis unit.

49. The urinalysis unit of claim 46, wherein said fluid transfer means includes a tube contained within said swing arm for carrying said urine sample from said urine sampling vessel to said urinalysis device.

50. The urinalysis unit of claim 49, wherein said fluid transfer means includes a pump in fluid communication with said tube for pumping said urine sample from said urine sampling device, through said tube, and to said urinalysis device.

51. The urinalysis unit of claim 50, wherein said fluid transfer means includes a rotary valve in cooperation with said pump for selectively discharging said urine sample from a pumping chamber of said pump into said toilet bowl and supplying said urine sample from said pumping chamber to said urinalysis device.

52. The urinalysis unit of claim 51, wherein said rotary valve cooperates with said pump to inject water into said pumping chamber and towards said toilet bowl.

53. The urinalysis unit of claim 46, wherein the frame includes a housing and a carrier liquid reservoir contained within said housing for holding a carrier liquid.

54. The urinalysis unit of claim 53, wherein said fluid transfer means includes a rotary valve in communication with a pump having a pumping chamber for selectively supplying said urine sample from said urine sampling vessel, through said pumping chamber, and towards said urinalysis device and supplying carrier liquid from said carrier liquid reservoir, through said pumping chamber, and towards said urinalysis device.

55. The urinalysis unit of claim 54, wherein said fluid transfer means includes a transfer tube between said rotary valve and said urinalysis unit for mixing said carrier liquid with said urine sample prior to said urine sample entering said urinalysis unit.

56. The urinalysis unit of claim 49, wherein said fluid transfer means includes at least one electrode within a cavity defined by said urine sampling device to detect whether said urine sample has accumulated within said urine sampling vessel.

57. The urinalysis unit of claim 56, wherein the fluid transfer means includes a pump, and the urinalysis unit includes control means for operating said pump of said fluid transfer means to transfer said urine sample through said tube and towards said urinalysis device in response to said electrode detecting said urine sample.

58. The urinalysis unit of claim 45, further comprising cleaning means positioned adjacent a rest position of said urine sampling device for flushing said urine sampling device with water.

59. The urinalysis unit of claim 58, wherein said rest position is between a toilet seat and an upper surface of a rim of said toilet bowl, said cleaning means including a nozzle operatively connected to a water supply for spraying water onto said urine sampling device.

60. The urinalysis unit of claim 28, wherein said urinalysis device includes a polarographic cell generating an electric signal in response to constituents of said urine sample.

61. The urinalysis unit of claim 60, wherein said polarographic cell includes an electrode supporting an enzyme for promoting a reaction with said constituents of said urine sample, said polarographic cell generating an electric signal representative of the product of said reaction.

62. The urinalysis unit of claim 60, wherein said polarographic cell includes a disposable polarographic flow cell for detachably mounting to a support socket connected to said housing.

63. The urinalysis unit of claim 62, wherein said support socket includes a fluid inlet and a fluid outlet, said fluid inlet being in communication with said fluid transfer means for receiving said urine sample and in communication with a carrier liquid reservoir for receiving a carrier liquid.

64. The urinalysis unit of claim 62, wherein said polarographic flow cell includes a base and an upper plate defining an electrolytic chamber, and a pair of passages in communication with said electrolytic chamber for supplying said urine sample and a carrier liquid to said electrolytic chamber.

65. The urinalysis unit of claim 62, wherein said urinalysis device includes data processing means responsive to said electric signal to determine the content of said constituents in said urine sample.

66. The urinalysis unit of claim 28, further comprising output means for outputting results of an analysis of said urine sample by said urinalysis device.

67. The urinalysis unit of claim 28, wherein said fluid transfer means includes a fluid pump having a pumping chamber, and a valve in communication with said pump, said valve having a first port in communication with said pumping chamber, a second port in communication with said urine sampling device, a third port in communication with a reservoir containing a liquid reagent, and a fourth port in communication with said urinalysis device, said valve selectively connecting said first port with said second port, third port, or fourth port to transfer a mixture of said urine sample and said liquid reagent to said urinalysis device.

68. The urinalysis unit of claim 45, wherein said urine sampling device includes a swing arm swingably mounted at a first end to said frame and a urine sampling vessel connected to a second end of said swing arm for collecting a urine sample, said fluid transfer means includes a pump and urine detection means within a cavity defined by said urine sampling device for detecting whether said urine sample has accumulated within said urine sampling device, and including control means for operating said pump to transfer said urine sample towards said urinalysis device in response to said urine detection means detecting said urine sample.

69. A toilet bowl fixture and urinalysis unit comprising
a toilet bowl fixture;
a urine sampling device including a collecting portion positionable in an inner space of the toilet bowl fixture for receiving a quantity of urine excreted into the bowl;
a urinalysis device;
fluid transfer means fluidly connecting the urine sampling device and the urinalysis device for transferring urine from the urine sampling device to the urinalysis device;
a support mounted on the toilet bowl fixture, the support including an open seating area and means for supporting the urine sampling device, the urinalysis device, and the fluid transfer means.

70. The toilet bowl fixture and urinalysis unit of claim 69, wherein the toilet bowl fixture includes seat mounting holes through which the support is mounted.

71. The toilet bowl fixture and urinalysis unit of claim 69, wherein the toilet bowl fixture includes a water closet bowl fixture having a bowl and a flushing water supply section located rearwardly of the bowl and the support is mounted on the toilet bowl fixture between the bowl and the flushing water supply section.

72. The toilet bowl fixture and urinalysis unit of claim 69, wherein the support includes a housing mounted on the toilet bowl fixture between the bowl and the flushing water supply section.

73. A method of collecting and analyzing a urine sample comprising the steps of:
positioning a urine sampling device into a predetermined urine sampling position in an inner space defined by a toilet bowl, said urine sampling device mounted to a toilet fixture and in fluid communication with a urinalysis device mounted to the toilet fixture, wherein a frame mounts to an underside of a toilet seat and a housing fixedly mounts to said toilet bowl, said housing for containing said urinalysis device, said urine sampling device being connected to said frame;
collecting a urine sample excreted into said urine sampling device;
detecting the presence of said urine sample within said urine sampling device;
transferring said urine sample from said urine sampling device to the urinalysis device mounted to the toilet fixture; and
analyzing the contents of said urine sample by said urinalysis device.

74. The method of claim 73, wherein said transferring step commences in response to the detection of said urine sample.

75. A method of collecting and analyzing a urine sample comprising the steps of:
positioning a urine sampling device into a predetermined urine sampling position in an inner space defined by a toilet bowl, said urine sampling device mounted to a toilet fixture and in fluid communication with a urinalysis device mounted to the toilet fixture, wherein a frame mounts to an underside of a toilet seat and a housing fixedly mounts to said toilet bowl, said housing for containing said urinalysis device, said urine sampling device being connected to said frame;
collecting a urine sample excreted into said urine sampling device;
transferring said urine sample from said urine sampling device to the urinalysis device mounted to the toilet fixture; and
analyzing the contents of said urine sample by said urinalysis device, wherein the analyzing step includes the substep of generating an electric signal in response to constituents of said urine sample, said electric signal being generated by a polarographic cell within the urinalysis device.

76. The method of claim 75, wherein the generating substep includes generating an electric signal representative of the product of a reaction between said constituents of said urine sample and an enzyme for promoting reaction with said constituents, said enzyme being supported by an electrode within said polarographic cell.

77. The method of claim 75, wherein the transferring step includes supplying said urine sample and a carrier liquid to an electrolytic chamber defined by a base and an upper plate of said polarographic flow cell, said urine sample and said carrier liquid being supplied through a pair of passages of said polarographic flow cell in fluid communication with said electrolytic chamber.

78. The method of claim 75, wherein the analyzing step includes the substep of processing said electric signal to determine the content of said constituents in said urine sample.

79. A method of collecting and analyzing a urine sample comprising the steps of:
positioning a urine sampling device into a predetermined urine sampling position in an inner space defined by a toilet bowl, said urine sampling device mounted to a toilet fixture and in fluid communication with a urinalysis device mounted to the toilet fixture;
collecting a urine sample excreted into said urine sampling device;
detecting the presence of said urine sample within said urine sampling device;
transferring said urine sample from said urine sampling device to the urinalysis device mounted to the toilet fixture;
generating an electric signal in response to constituents of said urine sample, said electric signal being generated by a polarographic cell within said urinalysis device; and
analyzing the contents of said urine sample by said urinalysis device, wherein the transferring step occurs in response to the detection of said urine sample within said urine sampling device, and the analyzing step is performed by data processing means within said urinalysis device.

* * * * *